(12) United States Patent
Kozlowski et al.

(10) Patent No.: US 7,851,565 B2
(45) Date of Patent: Dec. 14, 2010

(54) STABILIZED POLYMERIC THIOL REAGENTS

(75) Inventors: Antoni Kozlowski, Huntsville, AL (US); Samuel McManus, Huntsville, AL (US)

(73) Assignee: Nektar Therapeutics, San Carlos, CA (US)

( * ) Notice: Subject to any disclaimer, the term of this patent is extended or adjusted under 35 U.S.C. 154(b) by 1096 days.

(21) Appl. No.: 11/316,051

(22) Filed: Dec. 21, 2005

(65) Prior Publication Data

US 2006/0135586 A1 Jun. 22, 2006

Related U.S. Application Data

(60) Provisional application No. 60/639,823, filed on Dec. 21, 2004.

(51) Int. Cl.
| C08G 75/00 | (2006.01) |
| C08F 283/00 | (2006.01) |
| C08L 81/00 | (2006.01) |
| A61K 31/415 | (2006.01) |

(52) U.S. Cl. ............ 525/535; 525/54.1; 528/373; 528/425; 514/398; 424/78.27

(58) Field of Classification Search ............... 525/54.1, 525/535; 528/425, 373; 424/78.27; 514/398
See application file for complete search history.

(56) References Cited

U.S. PATENT DOCUMENTS

| 5,446,090 A | 8/1995 | Harris |
| 5,516,703 A | 5/1996 | Caldwell et al. |
| 5,580,923 A | 12/1996 | Yeung |
| 5,932,462 A | 8/1999 | Harris et al. |
| 6,306,584 B1 | 10/2001 | Bamdad |
| 2004/0167287 A1 | 8/2004 | Kozlowski |
| 2004/0204548 A1 | 10/2004 | Kozlowski |
| 2005/0014903 A1 | 1/2005 | Kozlowski |

FOREIGN PATENT DOCUMENTS

| CN | 1511861 A | 7/2004 |
| EP | 1 609 491 | 12/2005 |
| WO | 2004/063250 | 7/2004 |

OTHER PUBLICATIONS

Abuchowski, et al., "Alteration of immunological properties of bovine serum albumin by covalent attachment of polyethylene glycol," *J. Biol. Chem.*, vol. 252 (11), pp. 3578-3581 (1977).

Akiyama, et al., "Selective Synthesis of Heterobifunctional Poly(ethylene glycol) Derivatives Containing Both Mercapto and Acetal Terminals," *Bioconjugate Chem.*, vol. 11, pp. 947-950 (2000).

(Continued)

*Primary Examiner*—Duc Truong
(74) *Attorney, Agent, or Firm*—Mark A. Wilson

(57) ABSTRACT

Disclosed are water soluble polymeric reagents comprising the structure POLY-[Y—S—W]$_x$, where POLY is a water soluble polymer; Y is a hydrocarbon-based spacer group, x is 1 to 25, and S—W is a thiol, protected thiol, or thiol-reactive derivative. Preferably, the water soluble polymer is a PEG polymer. Also disclosed are conjugates of such polymeric reagents with pharmaceutically relevant molecules, and methods of their formation and use.

19 Claims, 2 Drawing Sheets

OTHER PUBLICATIONS

Bettinger, et al., "Convenient Polymer-Supported Synthesic Route to Heterobifunctional Polyethylene Glycols," *Bioconjugate Chem.*, vol. 9, pp. 842-846 (1998).

Chapman, et al., "PEGylated antibodies and antibody fragments for improved therapy: a review," *Adv. Drug Del. Rev.*, vol. 54, pp. 531-545 (2002).

Davis, et al., "Alteration of the circulating life and antigenic properties of bovine adenosine deaminase in mice by attachment of polyethylene glycol," *Clin. Exp. Immunol.*, vol. 46(3), pp. 649-652 (1981).

Harris, et al., "Synthesis of Polyethylene Glycol Thiol," *Polym. Preper.* (Am. Chem. Soc., Div. Polym. Chem), 32(1), pp. 154-155 (1991).

Herman, et al., "End-group modification of a-hydro-w-methoxy-poly(oxyethylene, 3a) Facile methods for the introduction of thiol-selective reactive end-group," Macromol. Chem. Phys., vol. 195, pp. 203-209 (1994).

Huang, et al., "A Polyethylene Glycol Copolymer for Carrying and Releasing Multiple Copies of Cysteine-Containing Peptides," Bioconjugate Chem., vol. 9, pp. 612-617 (1998).

Kaiser, et al., "Basic Studies on Heterobifunctional Biotin-PEG Conjugates with a 3-(4-Pyridyldithio)propionyl Marker on the Second Terminus." *Bioconjugate Chem.*, vol. 8, pp. 545-551 (1997).

Li, et al., "Chemical Modification of Surface Active Poly(ethylene oxide)-Poly(propylene oxide) Triblock Copolymers," *Bioconjugate Chem.*, vol. 7, pp. 592-599 (1996).

Musu, et al., "Reversible Modification of Thoil-Containing Polypeptides with Poly(ethylene glycol) Through Formation of Mixed Disulfide Bonds: The Case of Papaya Proteinase III," *Applied Biochem. And Biotech.*, vol. 56, pp. 243-263 (1996).

Otsuka, et al., "Quantitative and Reversible Lectin-Induced Association of Gold Nanoparticles Modified with a-Lactosyl-w-mercapto-poly(ethylene glycol)," *J. Am. Chem. Soc.*, vol. 123, pp. 8226-8230 (2001).

Suszki, et al., "Physicochemical and Biological Properties of Poly(Ethylene Glycol) Coupled Immunoglobulin G," *Biochimica et BioPhysica Acta*, vol. 788, pp. 248-255 (1984).

Svedhem, S., et al., "Synthesis of a Series of Oligo(ethylene glycol)-Terminated Alkanethiol Amides Designed to Address Structure and Stability of Biosensing Interfaces," *J. Org. Chem.*, vol. 66 (13), pp. 4494-4503 (2001).

Valiokas, R., Ostblom, M., Svedhem, S., Svensson, S. C. T. and Liedberg, B. (2000). "Temperature-driven phase transitions in oligo(ethylene glycol)- terminated self-assembled monolayers." Journal of Physical Chemistry B 104(32): 7565-7569.

Valiokas, R., Svedhem, S., Svensson, S. C. T. and Liedberg, B. (1999). "Self-assembled monolayers of oligo(ethylene glycol)-terminated and amide group containing alkanethiolates on gold." LANGMUIR 15(10): 3390-3394.

Zalipsky, "Functionalized Poly(ethylene glycol) for Preparation of Biologically Relevant Conjugates," *Bioconjugate Chem.*, vol. 6, pp. 150-165 (1995).

Zalipsky, et al., "New Detachable Poly(ethylene glycol) Conjugates: Cysteine-Cleavable Lipopolymers Regenerating Natural Phospholipid, Diacyl Phosphatidylethanolamine," *American Chem. Society*, vol. 10, No. 5, pp. 703-707 (1999).

Enzon Pharmaceuticals: Molecular Engineering Technologies, pp. 1-14 (Catalog 2004).

Nektar Transforming Therapeutics, Polyethylene Glycol and Derivatives for Advanced PEGylation, pp. 1-21 (Catalog 2003).

Nektar Transforming Therapeutics, Polyethylene Glycol and Derivatives for Advanced PEGylation, pp. 1-24 (Catalog 2004).

NOF Corporation, PEG Derivatives Phospholipid and Drug Delivery Materials for Pharmaceuticals, pp. 2-46 (Catalog 2003-1$^{st}$).

NOF Corporation, PEG Derivatives Phospholipid and Drug Delivery Materials for Pharmaceuticals, pp. 2-50 (Catalog 2003-2nd).

Polypure—products listing, pp. 1-5, (Apr. 2004).

Polypure—products listing, pp. 1-5, (Apr. 2005).

Quanta Biodesign, Labeling, Derivatization and Crosslinking Reagents for Biological and Related Materials with dPEG™ , pp. 2-38 (Catalog—Mar. 2004).

Quanta Biodesign, Labeling, Derivatization and Crosslinking Reagents incorporating our unique monodispersed dPEG™ Technology, pp. 2-31 (Catalog—Nov. 2004).

Quanta Biodesign, Inc., Product Catalog, pp. 1-51 (Catalog Jul. 2005).

Quanta Biodesign, Inc., Product Catalog, pp. 1-51 (Catalog Nov. 2005).

Shearwater Polymers, Inc., Product Listing, pp. 1-49 (Catalog 1995).

Shearwater Polymers, Inc., Polyethylene Glycol Derivatives, pp. 1-53 (Catalog 1997-1998).

Shearwater Polymers, Inc., Polyethylene Glycol Derivatives, pp. 1-50 (Catalog 2000).

Shearwater Corporation, Polyethylene Glycol Derivatives for Biomedical Applications, pp. 1-17 (Catalog 2001).

Cammas, et al., "Heterobifunctional Poly(ethylene oxide): Synthesis of α-Methoxy-α-amino and α-Hydroxy-α-amino PEOs with the Same Molecular Weights", Bioconjugate Chemistry, 1995; pp. 226-230, vol. 6.

Nabeshima, et al., "Remarkably Selective Ag+ Extraction and Transport by Thiolariat Ethers", J. Org. Chem., 1996; pp. 4342-4350, vol. 61.

Woghiren, et al., "Protected Thiol-Polyethylene Glycol: A New Activated Polymer for Reversible Protein Modification", Bioconjugate Chemistry, 1993; pp. 314-318, vol. 4.

Chinese Office Action dated Jul. 3, 2009, corresponding to Chinese Patent Application No. 200580047507.1.

Examination Report dated Mar. 17, 2008, corresponding to European Patent Application No. 05 855 832.1-1216.

Notication of Transmittal of the International Search Report and the Written Opinion of the International Searching Authority, or the Declaration, corresponding to PCT Application No. PCT/US2005/047337, filed Dec. 21, 2005, date of mailing Apr. 16, 2007.

Notification Concerning Transmittal of International Preliminary Report on Patentability, corresponding to PCT Application No. PCT/US2005/047337, filed Dec. 21, 2005, date of mailing Jul. 5, 2007.

STABILIZED POLYMERIC THIOL REAGENTS

CROSS REFERENCE TO RELATED APPLICATIONS

This application claims priority to U.S. Provisional Application Ser. No. 60/639,823, filed Dec. 21, 2004, and U.S. Provisional Application Ser. No. 60/705,968, filed Aug. 4, 2005, each which is hereby incorporated by reference in its entirety.

FIELD OF THE INVENTION

The present invention relates to stabilized polymeric thiol reagents derived from water-soluble polymers such as polyethylene glycol. In particular, the invention relates to the polymeric thiol reagents, conjugates thereof, and methods for utilizing such conjugates.

BACKGROUND OF THE INVENTION

Due to recent advances in biotechnology, therapeutic proteins and other biomolecules, e.g. antibodies and antibody fragments, can now be prepared on a large scale, making such biomolecules more widely available. Unfortunately, the clinical usefulness of potential therapeutic biomolecules in unmodified form is often hampered by their rapid proteolytic degradation, instability upon manufacture, storage or administration, or by their immunogenicity. These deficiencies can often be overcome by covalent attachment of a water-soluble polymer, such as polyethylene glycol (PEG). See, for example, Abuchowski, A. et al., *J. Biol. Chem.* 252(11):3579 (1977); Davis, S. et al., *Clin. Exp Immunol.* 46:649-652 (1981). The biological properties of PEG-modified proteins, also referred to as PEG-conjugates or PEGylated proteins, have been shown, in many cases, to be considerably improved over those of their non-PEGylated counterparts (Herman et al., *Macromol. Chem. Phys.* 195:203-209 (1994)). Polyethylene glycol-modified proteins have been shown to possess longer circulatory times in the body, due to increased resistance to proteolytic degradation, and also to possess increased thermostability (Abuchowski, A. et al., *J. Biol. Chem.* 252: 3582-3586 (1977). A similar increase in bioefficacy is observed with other biomolecules, e.g. antibodies and antibody fragments (Chapman, A., *Adv. Drug Del. Rev.* 54:531-545 (2002)).

Polyethylene glycol having activated end groups suitable for reaction with amino groups are commonly used for modification of proteins. Such activated PEGs or "polymeric reagents" include PEG-aldehydes (Harris, J. M. and Herati, R. S., *Polym Prepr. (Am. Chem. Soc., Div. Polym. Chem.)* 32(1):154-155 (1991)), mixed anhydrides, N-hydroxysuccinimide esters, carbonylimidazolides, and chlorocyanurates (Herman, S. et al., *Macromol. Chem. Phys.* 195:203-209 (1994)). In some cases, however, polymer attachment through protein amino groups can be undesirable, such as when derivatization of specific lysine residues inactivates the protein (Suzuki, T. et al., *Biochimica et Biophysica Acta* 788:248-255 (1984)). Therefore, it would be advantageous to have additional methods for the modification of a protein by PEG using another target amino acid for attachment, such as cysteine. Attachment to protein thiol groups on cysteine offers an advantage in that cysteines are typically less abundant in proteins than lysines, thus reducing the likelihood of protein deactivation upon conjugation to these thiol-containing amino acids. Thiol-selective activated polymers are described, for example, in commonly owned PCT publication no. WO 2004/063250.

Polymeric thiol derivatives, and specifically PEG thiols, are one type of thiol-selective activated polymer. However, many prior art polymeric thiols suffer from being highly susceptible to oxidative coupling to form disulfides, a degradative process that reduces the active component and adds difficult-to-remove impurities. The latter can be particularly problematic in the preparation of bioconjugates from these materials. Therefore, it would be advantageous to provide polymeric thiol reagents having enhanced stability over prior art reagents.

SUMMARY OF THE INVENTION

In one aspect, the invention provides a water-soluble activated polymer, also referred to as a "polymeric reagent," having the structure

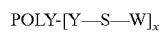

POLY-[Y—S—W]$_x$ wherein:

POLY is a water soluble polymer;

Y is a divalent linking group, containing at least four carbon atoms, consisting of a saturated or unsaturated hydrocarbon backbone which is three to eight carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group;

S is a sulfur atom attached to an sp$^3$ hybridized carbon of Y;

x is 1 to 25; and

S—W is a thiol, protected thiol, or thiol-reactive thiol derivative. In one embodiment, S—W is a thiol-reactive derivative, such as ortho-pyridyl disulfide (OPSS).

When x is 2, the reagent is a difunctional polymeric reagent, such as described further below, and it may have a linear or a "forked" morphology, as described herein. The polymeric reagent may also have a "multiarmed" morphology, as described herein, particularly when x is 3 or greater. In selected embodiments, x is 1 to 8, 1 to 6, or 1 to 4; in further embodiments, x is 1 or 2, or x is 1. The POLY component of the disclosed polymeric reagents can itself have a morphology selected from the group consisting of linear, branched, multi-armed, and combinations thereof, as described further herein.

In a particular embodiment, when POLY is a linear polyethylene glycol and Y is a linear alkyl chain, POLY has a molecular weight of at least 500.

In further embodiments, POLY has a molecular weight of at least 1000, or at least 2000. As an upper range, POLY has a molecular weight of not greater than 300,000 Da.

The "hydrocarbon backbone" of the linking group Y is more particularly defined as the shortest contiguous carbon chain connecting POLY and S. When the backbone of Y is unsaturated, it is preferably monounsaturated, i.e. having a single double or triple carbon-carbon bond. Preferably, the spacer group Y, including backbone and substituents, is monounsaturated or, more preferably, fully saturated. In another embodiment, the spacer group Y, including backbone and substituents, consists of saturated and aromatic portions.

Preferably, the backbone is saturated. For example, Y may be of the form —(CR$^1$R$^2$)$_n$—, where n is 3 to 8, and each of R$^1$ and R$^2$ is independently selected from hydrogen, lower alkyl, lower alkenyl, and a non-interfering substituent, where two groups $R^1$ and $R^2$ on different carbon atoms may be linked to form a cycloalkyl or aryl group. In selected embodiments, n is 3 to 6, n is 4 to 6, or n=4, and each of $R^1$ and $R^2$ is independently selected from hydrogen and lower alkyl, where lower alkyl is preferably methyl or ethyl.

In further selected embodiments, Y is selected from the group consisting of $C_4$-$C_8$ alkylene, $C_5$-$C_8$ cycloalkylene, and combinations thereof, any of which may include one or more non-interfering substituents.

Preferably, at most one or two non-interfering substituents, selected from the group consisting of $C_3$-$C_6$ cycloalkyl, halo, cyano, lower alkoxy, and phenyl, and preferably selected from methoxy, ethoxy, fluoro, and chloro, are included. In one embodiment, no heteroatom-containing substituents are present; that is, the linking Y consists of carbon and hydrogen.

In one preferred embodiment, each of $R^1$ and $R^2$ is hydrogen with respect to the n iterations of —$(CR^1R^2)$—; in another preferred embodiment, each of $R^1$ and $R^2$ is hydrogen with the exception of $R^1$ on a carbon adjacent said sulfur atom, said $R^1$ being lower alkyl, preferably methyl or ethyl (α-branching). In one embodiment, the α-branch group is methyl.

In embodiments of Y where Y is —$(CR^1R^2)n$- and two groups $R^1$ and $R^2$ on different carbon atoms are linked to form a cycloalkyl, cycloalkenyl, or aryl group, the cycloalkyl group is preferably a cyclopentyl or cyclohexyl group. Preferably, S is linked to an $sp^3$ hybridized acyclic carbon of Y in such embodiments.

As noted above, POLY may be a polyethylene glycol (PEG). Such a PEG typically has a molecular weight of 148 (e.g. a trimer plus linking oxygen atom) to about 200 to about 100,000 Daltons. In selected embodiments, the polyethylene glycol has a molecular weight from about 200 to about 40,000 Daltons. Representative molecular weights include, for example, 500, 1000, 2000, 2500, 3500, 5000, 7500, 10000, 15000, 20000, 25000, 30000, and 40000 Daltons. The PEG component of the disclosed reagents can itself have a morphology selected from the group consisting of linear, branched, multi-armed, and combinations thereof, as described further herein.

Accordingly, the invention provides a water soluble polymeric reagent comprising the structure:

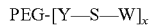

wherein:
PEG is a polyethylene glycol polymer;
Y is a divalent linking group consisting of a saturated or unsaturated hydrocarbon backbone which is three to eight carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group;
S is a sulfur atom attached to an $sp^3$ hybridized carbon of Y;
x is 1 to 25;
S—W is a thiol, protected thiol, or thiol-reactive thiol derivative; and
PEG has a molecular weight of at least 500 when PEG is linear, x is 1, and Y is a linear alkyl chain.

As stated above, when x is 2, the reagent is a difunctional polymeric reagent, such as described further below, and it may have a linear or a "forked" morphology, as described herein. The polymeric reagent may also have a "multiarmed" morphology, as described herein, particularly when x is 3 or greater. In selected embodiments, x is 1 to 8, 1 to 6, or 1 to 4; in further embodiments, x is 1 or 2, or x is 1. The PEG component of the disclosed reagents can itself have a morphology selected from the group consisting of linear, branched, multi-armed, and combinations thereof, as described further herein.

In preferred embodiments, PEG has a molecular weight of at least 148, at least 200, at least 500, at least 1000, or at least 2000, up to about 100,000 Daltons, including the various ranges noted above, and a morphology selected from linear, branched, forked, and multiarmed. S—W is preferably a thiol-reactive thiol derivative, and more preferably orthopyridyl disulfide (OPSS).

The "hydrocarbon backbone" of the linking group Y is more particularly defined as the shortest contiguous carbon chain connecting PEG and S. Preferably, the backbone of the linking group Y is saturated, such that Y has the formula —$(CR^1R^2)n$-, where n is 3 to 8, and each of $R^1$ and $R^2$ is independently selected from hydrogen, lower alkyl, lower alkenyl, and a non-interfering substituent, where two groups $R^1$ and $R^2$ on different carbon atoms may be linked to form a cycloalkyl or aryl group. In selected embodiments, n is 3 to 6, n is 4 to 6, or n=4, and each of $R^1$ and $R^2$ is independently selected from hydrogen and methyl.

In further selected embodiments, Y is selected from the group consisting of $C_3$-$C_8$ alkylene, $C_5$-$C_8$ cycloalkylene, and combinations thereof, any of which may include one or more non-interfering substituents, as described above. Preferably, at most one or two non-interfering substituents, selected from the group consisting of $C_3$-$C_6$ cycloalkyl, halo, cyano, lower alkoxy, and phenyl, and preferably selected from methoxy, ethoxy, fluoro, and chloro, are included. In one embodiment, no heteroatom-containing substituents are present; that is, the linking group Y consists of carbon and hydrogen.

As above, in one preferred embodiment, each of $R^1$ and $R^2$ is hydrogen with respect to the n iterations of —$(CR^1R^2)$—; in another preferred embodiment, each of $R^1$ and $R^2$ is hydrogen with the exception of $R^1$ on a carbon adjacent said sulfur atom, said $R^1$ being lower alkyl, preferably methyl or ethyl (α-branching). In one embodiment, the α-branch group is methyl.

In embodiments of Y where Y is —$(CR^1R^2)n$- and two groups $R^1$ and $R^2$ on different carbon atoms are linked to form a cycloalkyl, cycloalkenyl, or aryl group, the cycloalkyl group is preferably a cyclopentyl or cyclohexyl group. Preferably, S is linked to an $sp^3$ hybridized acyclic carbon of Y in such embodiments.

In an exemplary reagent of the form PEG-Y—S—W, Y is —$(CR^1R^2)n$- where each of $R^1$ and $R^2$ is hydrogen and n is 4, S—W is ortho-pyridyl disulfide (OPSS), and PEG is a methoxy-terminated polyethylene glycol (mPEG). The mPEG preferably has a molecular weight in the range of 5000 to 30000 Da. In further exemplary reagents, PEG and SW are similarly defined, n is 3 or 4, and each of $R^1$ and $R^2$ is hydrogen with the exception of $R^1$ on a carbon adjacent said sulfur atom, said $R^1$ being methyl (i.e., Y is —$CH_2CH_2CH(CH_3)$— or —$CH_2CH_2CH_2CH(CH_3)$—).).

The water soluble polymeric reagents may have a polyfunctional structure, as shown:

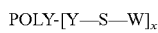

wherein:
POLY is a water soluble polymer;
x is 2 to 25;
each Y is a divalent linking group, having at least four carbon atoms, consisting of a saturated or unsaturated hydrocarbon backbone which is three to ten, preferably three to eight, carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group;

each S is a sulfur atom attached to an sp³ hybridized carbon of the adjacent Y; and each S—W is a independently a thiol, protected thiol, or thiol-reactive thiol derivative.

Preferably, the two or more Y groups are identical; the two or more W groups are also typically identical. Alternatively, particularly in a difunctional reagent (x=2), the two SW's may be different; e.g. one SW is a thiol or protected thiol while the other is a thiol-reactive derivative, or one SW is a thiol or thiol-reactive derivative while the other is a protected thiol.

As noted above, when x is 2, the polymeric reagent may have a linear or a "forked" morphology, as described herein. The polymeric reagent may also have a "multiarmed" morphology, as described herein, particularly when x is 3 or greater. In selected embodiments, x is 2 to 8, 2 to 6, or 2 to 4; in one embodiment, x is 2. The POLY component of the disclosed reagents can itself have a morphology selected from the group consisting of linear, branched, multi-armed, and combinations thereof, as described further herein.

As above, the backbone of Y is preferably saturated, such that each Y is a linker having at least four carbon atoms and having the formula —(CR¹R²)n-, where n is 3 to 10, preferably 3 to 8, and each of R¹ and R² is independently selected from hydrogen, lower alkyl, lower alkenyl, and a non-interfering substituent, where two groups R¹ and R² on different carbon atoms may be linked to form a cycloalkyl or aryl group. Further preferred embodiments of Y, and of POLY, are generally as defined above for the monomeric reagent POLY-Y—S—W.

The corresponding PEG-based polyfunctional polymeric reagents have the structure:

PEG-[Y—S—W]$_x$ wherein:
PEG is polyethylene glycol polymer;
x is 2 to 25;
each Y is a divalent linking group consisting of a saturated or unsaturated hydrocarbon backbone which is three to ten, preferably three to eight, carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group;

each S is a sulfur atom attached to an sp³ hybridized carbon of the adjacent Y; and each S—W is a independently a thiol, protected thiol, or thiol-reactive thiol derivative.

Preferably, the multiple Y groups are identical; the multiple W groups are also typically identical. The backbone of Y is preferably saturated, such that each Y is a linker having the formula —(CR¹R²)n-, where n is 3 to 10, preferably 3 to 8, and each of R¹ and R² is independently selected from hydrogen, lower alkyl, lower alkenyl, and a non-interfering substituent, where two groups R¹ and R² on different carbon atoms may be linked to form a cycloalkyl or aryl group.

Further preferred embodiments of Y, and of PEG, are generally as defined above for PEG-[Y—S—W]$_x$. In an exemplary difunctional reagent of the form W—S—Y-PEG-Y—S—W, each Y is —(CR¹R²)n- where each of R¹ and R² is hydrogen and n is 4, S—W is ortho-pyridyl disulfide (OPSS), and each PEG is a methoxy-terminated polyethylene glycol (mPEG). The mPEG preferably has a molecular weight in the range of 1000 to 5000 Da, e.g. about 2000 or about 3400 Da. In a further exemplary reagent, PEG and SW are similarly defined, n is 3 or 4, and each of R¹ and R² is hydrogen with the exception of R¹ on a carbon adjacent said sulfur atom, said R¹ being methyl.

In a related aspect, the invention provides a polymer conjugate comprising the structure:

POLY-[Y—S—S-A]$_x$ wherein:
POLY is a water soluble polymer;
x is 1 to 25;
Y is a divalent linking group consisting of a saturated or unsaturated hydrocarbon backbone which is three to ten, preferably three to eight, carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group;

S—S is a disulfide group attached to an sp³ hybridized carbon of Y; and

A is a covalently linked residue (as defined herein) of a pharmacologically active molecule.

In selected embodiments, x is 1 to 8, 1 to 6, or 1 to 4; in further embodiments, x is 1 or 2, or x is 1. When x is 2, the conjugate may have a linear or a "forked" morphology, as described herein. The conjugate may also have a "multiarmed" morphology, as described herein, particularly when x is 3 or greater. The POLY component of the conjugate can itself have a morphology selected from the group consisting of linear, branched, multi-armed, and combinations thereof, as described further herein.

Preferably, the multiple Y groups are identical. The hydrocarbon backbone of Y is preferably saturated, with Y having the formula —(CR¹R²)n-, where n is 3 to 10, preferably 3 to 8, each of R¹ and R² is independently selected from hydrogen, alkyl, alkenyl, and a non-interfering substituent, and where two groups R¹ and R² on different carbon atoms may be linked to form a cycloalkyl or aryl group. More preferably, Y is selected from the group consisting of C₃-C₈ alkylene, C₅-C₈ cycloalkylene, aryl, and combinations thereof, any of which may include one or more non-interfering substituents. In one embodiment, Y has at least four carbon atoms.

In further embodiments, Y is a linear or branched alkylene having the formula —(CR¹R²)n-, where n is 3 to 10, and each of R¹ and R² is independently selected from hydrogen, lower alkyl, lower alkenyl, and a non-interfering substituent. More preferably, n is 3 to 8, or 3 to 6, and each of R¹ and R² is independently selected from hydrogen and methyl. In selected embodiments, each of R¹ and R² is hydrogen. In another preferred embodiment, each of R¹ and R² is hydrogen with the exception of R¹ on a carbon adjacent said disulfide linkage, said R¹ being lower alkyl, e.g. methyl or ethyl.

Other embodiments include those in which Y is —(CR¹R²) n-, where n is 3 to 10, preferably 3 to 8, and two groups R¹ and R² on different carbon atoms are linked to form a cycloalkyl or aryl group, preferably a cycloalkyl such as cyclopentyl or cyclohexyl group.

The water soluble polymer POLY preferably has a molecular weight of at least 500, or at least 1000. The molecular weight of POLY is typically greater than 200 and less than about 300K Daltons, preferably less than about 200K Daltons, and more preferably less than about 100 K Daltons. In one embodiment, POLY is a polyethylene glycol, preferably having a molecular weight of 148 to about 200 to about 100,000 Daltons, and a morphology selected from linear, branched, forked, and multiarmed. In selected embodiments, the polyethylene glycol has a molecular weight from about 200 to about 40,000 Daltons. Representative molecular weights include, for example, 500, 1000, 2500, 3500, 5000, 7500, 10000, 15000, 20000, 25000, 30000, and 40000 Daltons.

The molecule conjugated to the water soluble polymer, represented by A in its conjugated form, has a reactive thiol group in its unconjugated form and is preferably selected from the group consisting of proteins, peptides, and small molecules, typically small organic molecules.

The conjugate is preferably itself water soluble. The conjugate may be provided in or with a suitable pharmaceutical excipient, such as an aqueous carrier, for therapeutic use.

In a related aspect, the invention provides a method for delivering a pharmacologically active molecule having a reactive thiol group to a subject, by administering to the subject a conjugate as described above, in a pharmaceutically acceptable carrier. The conjugate is typically prepared by conjugating the molecule with any of the water soluble polymeric reagents described herein.

The hydrocarbon-based segment(s), Y, in the activated polymeric reagents of the invention, being hydrophobic in nature, are effective to reduce the tendency towards dimerization of these reagents, relative to prior art reagents in which the thiol is linked to a heteroatom in the polymer segment (or in a linking moiety) by, for example, a two-carbon linkage. Branching of Y at the carbon adjacent to the sulfur atom (α-branching) is further effective to reduce dimerization. The hydrocarbon-based segment Y also reduces cleavage, e.g. enzymatic cleavage in vivo, of the adjacent disulfide bond, in conjugates formed using these reagents.

The reagents disclosed herein are further characterized as being "linkerless" reagents; that is, the water-soluble polymer, preferably a PEG, is directly linked to the hydrocarbon-based spacer group Y. The absence of heteroatom-containing linkages, such as amides, esters, or carbamates, between the active conjugating functionality, i.e. the thiol or protected thiol, and the polymer reduces the potential for degradation of the resulting conjugate. Moreover, the presence of these linkages, such as amides, in such reagents can trigger a deleterious immune response. This potential is eliminated or greatly reduced by use of the current "linkerless" reagents.

As shown in Example 2 herein, a polymeric thiol reagent of the invention was more stable under synthetic conditions than a corresponding reagent having only a two-carbon linker between the hydrophilic polymer (PEG) and thiol group. This increased stability is also exhibited in Example 9 and comparative Example 10. The conjugation behavior of the polymeric thiol reagent of the invention was similar to that observed for a polymeric reagent (a maleimide-terminated polymer) known not to dimerize, as also shown in Example 2.

These and other objects and features of the invention will become more fully apparent when the following detailed description of the invention is read in conjunction with the accompanying drawings.

DETAILED DESCRIPTION OF THE INVENTION

Definitions

Figure 1:
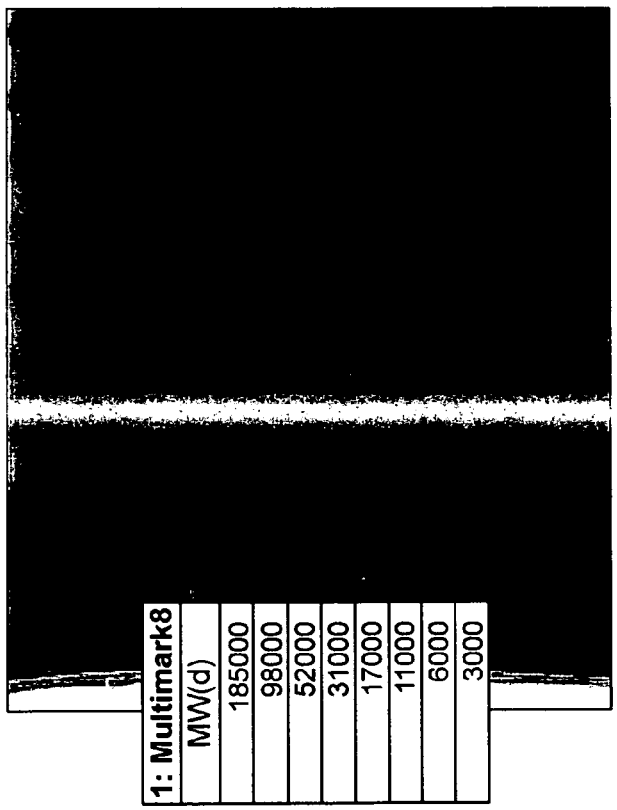
FIG. 1 shows a PAGE analysis of a conjugation reaction between a polymeric reagent of the invention, designated mPEG$_{5000}$-4C-OPSS, as described in Examples 1-2, with reduced BSA, and the corresponding conjugation reaction of the polymeric reagent mPEG$_{5000}$-maleimide with reduced BSA: Lane 1, standards; Lane 2, reduced BSA; Lane 3, conjugation with mPEG-MAL; Lane 4, conjugation with mPEG-4C-OPSS. The gel is stained with SimplyBlue Safe Stain.

The following terms as used herein have the meanings indicated. As used in the specification, and in the appended claims, the singular forms "a," "an," "the," include plural referents unless the context clearly dictates otherwise.

"PEG" or "polyethylene glycol," as used herein, is meant to encompass any water soluble poly(ethylene oxide). Typically, PEGs for use in the present invention will comprise one of the two following structures: —CH$_2$CH$_2$O(CH$_2$CH$_2$O)$_m$—CH$_2$CH$_2$— or —O(CH$_2$CH$_2$O)$_m$—, where m is generally from 2 to about 6000, more typically 4 or 5 to about 2500. In a broader sense, "PEG" can refer to a polymer that contains a majority, i.e., greater than 50%, of subunits that are —CH$_2$CH$_2$O—. Preferably, greater than 75%, greater than 95%, or substantially all of the monomeric subunits are —CH$_2$CH$_2$O—. The terminal groups and architecture of the overall PEG may vary. One terminus of the PEG may contain an end-capping group, which is generally a carbon-containing group comprised of 1-20 carbons and is preferably selected from alkyl, alkenyl, alkynyl, aryl, aralkyl, cycloalkyl, heterocyclo, and substituted forms of any of the foregoing. The end-capping group can also be a silane. An end-capping group is one that does not readily undergo chemical transformation under typical synthetic reaction conditions. Most preferred are alkyl (alkoxy) or aralkyl (aralkoxy) capping groups, such as methyl, ethyl or benzyl.

The end-capping group can also advantageously comprise a phospholipid. When the polymer has an end-capping group such as a phospholipid, unique properties (such as the ability to form organized structures with similarly end-capped polymers) are imparted to the polymer. Exemplary phospholipids include, without limitation, those selected from the class of phospholipids called phosphatidylcholines. Specific phospholipids include, without limitation, those selected from the group consisting of dilauroyl phosphatidylcholine, dioleyl phosphatidylcholine, dipalmitoyl phosphatidylcholine, distearoyl phosphatidylcholine, behenoyl phosphatidylcholine, arachidoyl phosphatidylcholine, and lecithin.

The end-capping group can also advantageously comprise a detectable label. Such labels include, without limitation, fluorescers, chemiluminescers, moieties used in enzyme labeling, colorimetric (e.g., dyes), metal ions, radioactive moieties, and the like.

The PEG may also be terminated with a functional group, such as those described below, preferably in protected form.

Specific PEG forms for use in the invention include PEGs having a variety of molecular weights, structures or geometries (e.g., branched, linear, forked, multiarmed).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, that for the purposes of the invention, is considered to possess a structure distinct from that of a branched polymer. A "branch point" refers to a bifurcation point comprising one or more atoms at which a polymer splits or branches from a linear structure into one or more additional polymer arms.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Water-soluble," in the context of a polymer of the invention or a "water-soluble polymer segment", is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

"Molecular mass" or "molecular weight" of a polymer, unless otherwise specified, refers to number average molecular weight. Number average molecular weight ($M_n$) is defined as $\Sigma N_i M_i / \Sigma N_i$, wherein $N_i$ is the number of polymer molecules (or the number of moles of those molecules) having molecular weight $M_i$. The number average molecular weight of a polymer can be determined by osmometry, end-group titration, and colligative properties. Weight average molecular weight is defined as $\Sigma N_i M_i^2 / \Sigma N_i M_i$, where $N_i$ is again the number of molecules of molecular weight $M_i$. The weight average molecular weight can be determined by light scattering, small angle neutron scattering (SANS), X-ray scattering, and sedimentation velocity.

The polymers of the invention, or employed in the invention, may be polydisperse; i.e., the number average molecular weight and weight average molecular weight of the polymers are not equal. However, the polydispersity values, expressed as a ratio of weight average molecular weight ($M_w$) to number average molecular weight ($M_n$), ($M_w/M_n$), are generally low; that is, less than about 1.2, preferably less than about 1.15, more preferably less than about 1.10, still more preferably less than about 1.05, yet still most preferably less than about 1.03, and most preferably less than about 1.025.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive" or "inert," with reference to a functional group present on a molecule in a reaction mixture, indicates that the group remains largely intact under conditions effective to produce a desired reaction in the reaction mixture.

A "protecting group" is a moiety that prevents or blocks reaction of a particular chemically reactive functional group in a molecule under certain reaction conditions. The term may also refer to the protected form of a functional group. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protected forms of such functional groups include, for carboxylic acids, esters (such as a p-methoxybenzyl ester), amides and hydrazides; for amino groups, carbamates (such as tert-butoxycarbonyl or fluorenylmethoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A "thiol-reactive derivative" of a thiol refers to a thiol derivative which can react with another thiol, preferably under conditions of moderate temperature and neutral or physiological pH, to form a disulfide linkage. Preferably, the reaction forms only stable byproducts. Typical examples of such derivatives are ortho-pyridyl disulfides and TNB-thiol derivatives (where TNB is 5-thio-2-nitrobenzoic acid). See e.g. Hermanson, *Bioconjugate Techniques*, Academic Press, 1996, pp 150-152.

As used herein, the term "functional group" or any synonym thereof is meant to encompass protected or derivatized forms thereof. Similarly, the term "thiol reagent" or "polymeric thiol" encompasses protected or derivatized thiol reagents or polymeric protected or derivatized thiols (such as polymer-OPSS).

A "physiologically cleavable" or "hydrolysable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides, thioesters, thiolesters, and carbonates. An "enzymatically degradable linkage" means a linkage that is subject to degradation by one or more enzymes.

"Substantially" or "essentially" means nearly totally or completely, for instance, 95%, 99% or greater of some given quantity.

"Alkyl" refers to a hydrocarbon chain, typically ranging from about 1 to 20 atoms in length. Such hydrocarbon chains are preferably but not necessarily saturated and may be branched or, preferably, linear (unbranched). Exemplary alkyl groups include ethyl, propyl, butyl, pentyl, 2-methylbutyl, 2-methylpropyl (isobutyl), 3-methylpentyl, and the like. As used herein, "alkyl" includes cycloalkyl when three or more carbon atoms are referenced. "Alkylene" refers to a divalent alkyl group, e.g. —$(CH_2)_x$—.

"Lower alkyl" refers to an alkyl group containing from 1 to 6 carbon atoms, more preferably 1 to 4 carbon atoms, as exemplified by methyl, ethyl, n-butyl, isopropyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8. "Cycloalkylene" refers to a divalent cycloalkyl group.

As used herein, "alkenyl" refers to a branched or unbranched hydrocarbon group having 2 to 15 carbon atoms and containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group having 2 to 15 atoms and containing at least one triple bond, such as ethynyl, n-propynyl, isopentynyl, n-butynyl, octynyl, decynyl, and so forth.

"Alkoxy" refers to an —OR group, wherein R is alkyl or substituted alkyl, preferably $C_1$-$C_{20}$ alkyl (e.g., methoxy, ethoxy, propyloxy, etc.), more preferably lower alkyl (i.e. $C_1$-$C_6$ or $C_1$-$C_4$).

"Aryl" refers to a substituted or unsubstituted monovalent aromatic radical having a single ring (e.g., phenyl) or two condensed or fused rings (e.g., naphthyl). Multiple aryl rings may also be unfused (e.g. biphenyl). The term includes heteroaryl groups, which are aromatic ring groups having one or more nitrogen, oxygen, or sulfur atoms in the ring, such as furyl, pyrrole, pyridyl, and indole.

"Aralkyl" refers to an alkyl, preferably lower ($C_1$-$C_4$, more preferably $C_1$-$C_2$) alkyl, substituent which is further substituted with an aryl group; examples are benzyl and phenethyl. "Aralkoxy" refers to a group of the form —OR where R is aralkyl; one example is benzyloxy.

A "heterocycle" refers to a ring, preferably a 5- to 7-membered ring, whose ring atoms are selected from the group consisting of carbon, nitrogen, oxygen and sulfur. Preferably, the ring atoms include 3 to 6 carbon atoms. Examples of aromatic heterocycles (heteroaryl) are given above; non-aromatic heterocycles include, for example, pyrrolidine, piperidine, piperazine, and morpholine.

A "substituted" group or moiety is one in which a hydrogen atom has been replaced with a non-hydrogen atom or group, which is preferably a non-interfering substituent.

"Non-interfering substituents" are those groups that, when present in a molecule, are typically non-reactive with other functional groups contained within the molecule.

These include, but are not limited to, lower alkyl, alkenyl, or alkynyl; lower alkoxy; $C_3$-$C_6$ cycloalkyl; halo, e.g., fluoro, chloro, bromo, or iodo; cyano; oxo (keto); nitro; and phenyl.

By "residue" is meant the portion of a molecule remaining after reaction with one or more molecules. For example, a biologically active molecule residue in a polymer conjugate of the invention typically corresponds to the portion of the biologically active molecule up to but excluding the covalent linkage resulting from reaction of a reactive group on the biologically active molecule with a reactive group on a polymer reagent.

The term "conjugate" refers to an entity formed as a result of covalent attachment of a molecule, e.g., a biologically active molecule, to a reactive polymer molecule, preferably a poly(ethylene glycol).

Each of the terms "drug," "biologically active molecule," "biologically active moiety," "biologically active agent", "pharmacologically active agent", and "pharmacologically active molecule", when used herein, means any substance which can affect any physical or biochemical property of a biological organism, where the organism may be selected from viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like. Also included are foods, food supplements, nutrients, nutraceuticals, drugs, vaccines, antibodies, vitamins, and other beneficial agents.

"Pharmaceutically acceptable excipient" or "pharmaceutically acceptable carrier" refers to an excipient that can be included in the compositions of the invention and that causes no significant adverse toxicological effects to a patient.

"Pharmacologically effective amount," "physiologically effective amount," and "therapeutically effective amount" are used herein to refer to mean the amount of a polymer-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "patient" refers to a living organism suffering from or prone to a condition that can be prevented or treated by administration of a biologically active agent or conjugate thereof, and includes both humans and animals.

Polymeric Thiol Reagents

The water-soluble, polymeric reagents of the invention comprise the structure

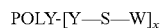

POLY-[Y—S—W]$_x$ wherein:

POLY is a water-soluble polymer segment;

x is 1 to 25;

Y is a divalent linking group comprising at least four carbon atoms, and consisting of a saturated or unsaturated hydrocarbon backbone which is three to eight carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group;

S is a sulfur atom attached to an $sp^3$ hybridized carbon of Y;

and S—W is a thiol (i.e. W is H), protected thiol, or thiol-reactive derivative.

In one embodiment, S—W is a thiol-reactive derivative, such as ortho-pyridyl disulfide (OPSS). Protected thiols include, for example, thioethers, such as S-benzyl or S-trityl ethers, and thioesters.

The sulfur atom S is attached to an sp hybridized carbon atom of Y, as noted, rather than to an aryl ring or double bond.

In one embodiment, the carbon atom to which the sulfur atom is attached has a lower alkyl substituent, such as methyl or ethyl (α-branching).

The "backbone" of the spacer group Y is more particularly defined as the shortest contiguous carbon chain connecting POLY and S. In one embodiment, the backbone of Y is saturated. For example, Y may be of the form —$(CR^1R^2)_n$—, where n is 3 to 8, preferably 3 to 6, each of $R^1$ and $R^2$ is independently selected from hydrogen, lower alkyl, lower alkenyl, and a non-interfering substituent, and where two groups $R^1$ and $R^2$ on different carbon atoms of —$(CR^1R^2)_n$— may be linked to form a cycloalkyl, cycloalkenyl, or aryl group. When Y contains a cycloalkyl group, it is preferably a five- or six-membered cycloalkyl group.

In selected embodiments, Y is selected from the group consisting of $C_3$-$C_8$ alkylene and combinations of $C_3$-$C_8$ alkylene with $C_5$-$C_8$ cycloalkylene or aryl, any of which may include one or more non-interfering substituents. Preferably, at most one or two non-interfering substituents, selected from the group consisting of $C_3$-$C_6$ cycloalkyl, halo, cyano, lower alkoxy, and phenyl, and preferably selected from methoxy, ethoxy, fluoro, and chloro, are included. In one embodiment, no heteroatom-containing substituents are present; that is, Y consists of carbon and hydrogen.

When the backbone of Y is unsaturated, it is preferably monounsaturated, i.e. having a single double or triple carbon-carbon bond. Preferably, the spacer group Y, including backbone and substituents, is monounsaturated or, more preferably, fully saturated. In this embodiment, Y may be a fully saturated hydrocarbon.

In another embodiment, the spacer group Y, including backbone and substituents, consists of saturated and aromatic portions, preferably saturated and aromatic hydrocarbon portions.

In the polymeric reagents, when Y is —$(CR^1R^2)_n$—, the polymer segment POLY preferably has a molecular weight of at least 500 Da when each of $R^1$ and $R^2$ is hydrogen with respect to the n iterations of —$(CR^1R^2)$—, particularly when POLY is a linear PEG and x=1 in the formula above. POLY may further have a molecular weight greater than 500 Da, greater than 750 Da, or greater than 1000 Da. A variety of greater molecular weight ranges, up to about 300,000 Da, more typically up to about 100,000 Da, can be used, as described above.

When x is 2, the reagent is a difunctional polymeric reagent, such as described further below, and it may have a linear or a "forked" morphology, as described herein. The polymeric reagent may also have a "multiarmed" morphology, as described herein, particularly when x is 3 or greater. In selected embodiments, x is 1 to 8, 1 to 6, or 1 to 4; in further embodiments, x is 1 or 2, or x is 1. The POLY component of the disclosed reagents can itself have a morphology selected from the group consisting of linear, branched, multi-armed, and combinations thereof, as described further herein.

In a preferred embodiment, the water soluble polymer segment is a polyethylene glycol, such that the reagent has the formula PEG-[Y—S—W]$_x$ wherein:

PEG is a poly(ethylene glycol);

Y is a divalent linking group consisting of a saturated or unsaturated hydrocarbon backbone which is three to eight carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group;

S is a sulfur atom attached to an $sp^3$ hybridized carbon of Y;

x is 1 to 25; and

S—W is a thiol (i.e. W is H), protected thiol, or thiol-reactive derivative.

The inventors have found that, by including a hydrophobic spacer group between the water-soluble polymer segment and the thiol group in a water-soluble polymeric thiol, the tendency of such a molecule to dimerize to form disulfides is reduced. Yields are accordingly increased in preparation of such reagents and in their conjugation with other molecules, as demonstrated below.

The spacer groups described herein are hydrocarbon-based groups more three carbons or more in length, which preferably contain at least four carbon atoms, which may include branching carbons (e.g. an isobutylene, or 1-methylpropylene, linkage). Although described as "hydrocarbon based", the spacer group may include a limited number of non-interfering substituents as defined herein. Preferably, however, the spacer group consists of carbon and hydrogen.

In preferred embodiments of the polymeric reagent, Y is a linear or branched alkylene having the formula —$(CR^1R^2)_n$—, where n is 3 to 8, and each of $R^1$ and $R^2$ is independently selected from hydrogen, lower alkyl, lower alkenyl, and a non-interfering substituent. Preferably, zero to two, more preferably zero or one, such non-interfering substituents are included.

Preferably, n is 4 to 8, more preferably 4 to 6. In one embodiment, each of $R^1$ and $R^2$ is independently selected from hydrogen and methyl. In a preferred embodiment, each of $R^1$ and $R^2$ is hydrogen with respect to the n iterations of —$(CR^1R^2)$—; in another preferred embodiment, each of $R^1$ and $R^2$ is hydrogen with the exception of $R^1$ on a carbon adjacent said sulfur atom (α-carbon), said $R^1$ being lower alkyl, preferably methyl or ethyl (α-branching). In one embodiment, the α-branch group is methyl.

In embodiments of Y where Y is —$(CR^1R^2)_n$—, n is 4 to 8, and two groups $R^1$ and $R^2$ on different carbon atoms are linked to form a cycloalkyl, cycloalkenyl, or aryl group, the cycloalkyl group is preferably a cyclopentyl or cyclohexyl group. In such embodiments, the sulfur atom is preferably attached to a non-cyclic carbon of Y.

Exemplary spacer groups Y having a saturated backbone include the following (where the curved lines indicate bonds to POLY or S, so that the first structure, for example, represents n-butylene):

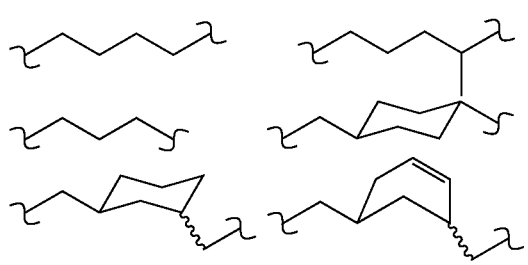

As noted above, the "backbone" of the spacer group is the shortest contiguous carbon chain linking POLY to the sulfur atom. Accordingly, each of the structures in the second row above has a five-carbon backbone. By this definition, moreover, the last structure shown has a saturated backbone, although the spacer group as a whole is unsaturated.

In one exemplary polymeric reagent, depicted below, POLY is methoxy-terminated polyethylene glycol (mPEG), Y is —(CH$_2$)$_4$—, and —S—W is ortho-pyridyl disulfide (OPSS), as depicted below, or SH. The mPEG preferably has a molecular weight in the range of 5000 to 30000 Da; e.g. about 5000, about 10000, about 20000, or about 30000 Da.

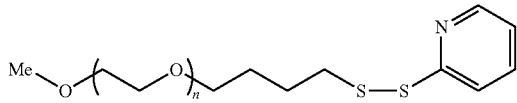

In a further embodiment, the polymeric reagent is a difunctional structure represented by W—S—Y-POLY-Y—S—W, where POLY, Y and S—W are as defined above. Typically, though not necessarily, the polymeric reagent is symmetrical. An exemplary polymeric reagent of this structure, depicted below, is one in which POLY is polyethylene glycol (PEG), each Y is —(CH$_2$)$_4$—, and each —S—W is ortho-pyridyl disulfide (OPSS), as depicted below, or SH. The PEG preferably has a molecular weight in the range of about 1000 to 5000 Da, e.g. 2000 or 3400 Da.

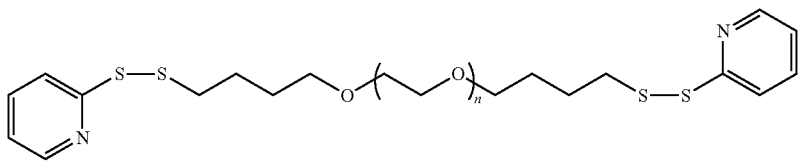

Further exemplary polymeric reagents include reagents of the general formula PEG-[Y—S—W]$_x$ where x is 1 or 2, Y is —(CH$_2$CH$_2$CH$_2$CH(CH$_3$))—, and S—W is SH or ortho-pyridyl disulfide (OPSS). When x is 1, PEG is preferably methoxy-terminated polyethylene glycol (mPEG). Such reagents are depicted below ("Me" represents methyl here and elsewhere):

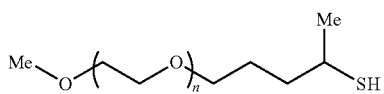
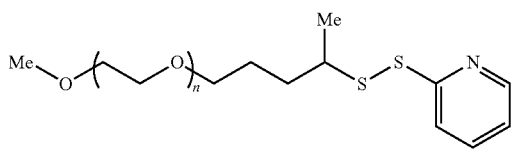
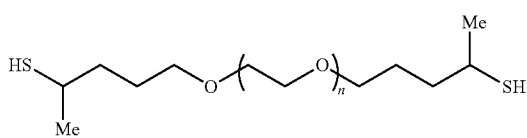
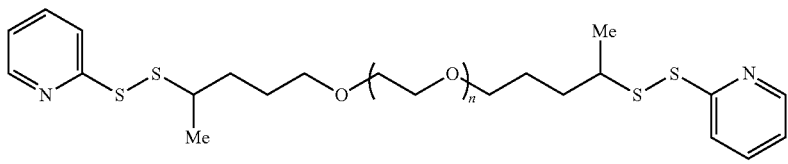

Further exemplary polymeric reagents include those of the general formula PEG-[Y—S—W]$_x$ where x is 1 or 2, Y is —(CH$_2$CH$_2$CH(CH$_3$))—, and S—W is SH or ortho-pyridyl disulfide (OPSS). When x is 1, PEG is preferably mPEG. Such reagents are depicted below:

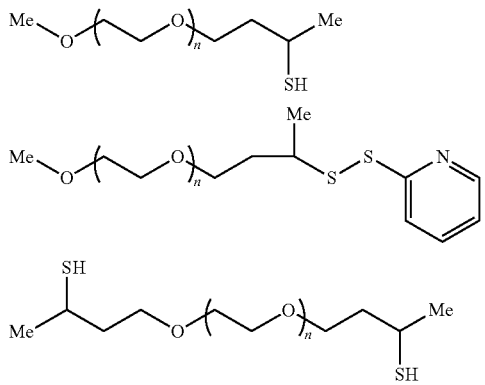

-continued

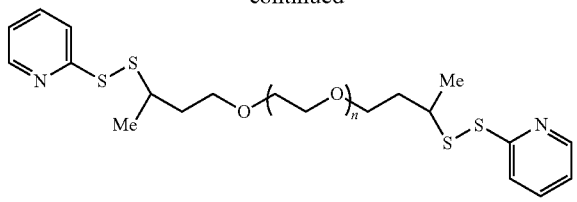

Another exemplary class of polymeric reagents is that of the general formula PEG-[Y—S—W]$_x$ where x is 1, Y is —(CH$_2$)$_4$—, —S—W is SH or ortho-pyridyl disulfide (OPSS), and PEG is terminated with the structure:

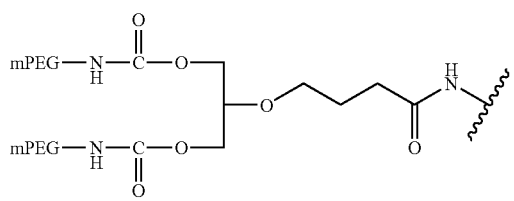

Such reagents are depicted generally below:

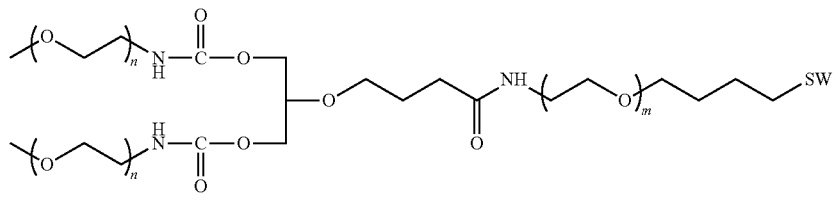

Preferably, the PEG attached to Y—SW has a molecular weight of about 500 Da or less, or about 200 Da or less, e.g. where m=2 to 10, preferably 2 to 4. In one embodiment, m=4. Each mPEG in the terminal branched structure shown preferably has a molecular weight of about 5 KDa to about 20 KDa; e.g. n=about 110 to about 450. Each mPEG may be, for example, 5, 10, 15 or 20 KDa in molecular weight.

The reagents described herein are characterized as being "linkerless" thiols; that is, where the water-soluble polymer is directly linked to the hydrocarbon-based spacer group Y. For example, the oxygen atom of a repeating alkylene glycol unit of a poly(alkylene)glycol, such as —CH$_2$CH$_2$O— in PEG, is directly linked to Y. The absence of additional heteroatoms, particularly in linkages such as esters, carbamates, or amides, between the active conjugating functionality, i.e., the thiol or protected thiol, and the polymer reduces the potential for degradation of the conjugated polymer. Moreover, the presence of such heteroatom-containing linkages, such as amides, in such reagents, can trigger a deleterious immune response. This potential is eliminated or greatly reduced by the current "linkerless" reagents.

In the polymeric reagents, the polymer segment POLY preferably has a molecular weight of at least 500 Da, particularly in embodiments where POLY is PEG. Various preferred embodiments of the polymer segment POLY are described in detail below. Preferably, the polymer segment "POLY" is a polyalkylene glycol, such as a polyethylene glycol (PEG). The polyethylene glycol may have various molecular weights, from about 88 to about 100,000 Daltons, within the stipulations above. In selected embodiments, the polyethylene glycol has a weight average molecular mass from 148 (e.g. a trimer plus linking oxygen atom) to about 200 to about 40,000 Daltons. Representative molecular weights include, for example, 500, 1000, 2000, 3000, 3500, 5000, 7500, 10000, 15000, 20000, 25000, 30000, and 40000 Daltons. Generally, difunctional or polyfunctional reagents will employ POLY or PEG segments of lower molecular weight than monofunctional reagents.

The polymer can have a structure selected from the group consisting of linear, branched, forked, multi-armed, and combinations thereof, as described further herein.

The Polymer Segment, POLY

Representative water soluble polymers for use in preparing the polymeric reagents of the invention include poly(alkylene glycols) such as poly(ethylene glycol), poly(propylene glycol) ("PPG"), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, and poly(N-acryloylmorpholine). POLY can be a homopolymer, an alternating copolymer, a random copolymer, a block copolymer, an alternating tripolymer, a random tripolymer, or a block tripolymer of any of the above. The water-soluble polymer segment is preferably a poly(ethylene glycol) ("PEG") or a derivative thereof.

Preferably, the polymer is a hydrophilic polymer; i.e., a polymer containing fewer than about 25 subunits of propylene oxide or other similar hydrophobic polymer segments. The polymer may, in an alternative embodiment, have no propylene oxide or similar hydrophobic subunits. In one instance, the polymer is preferably not a pluronic-type polymer. In yet another particular embodiment, the polymer is preferably not bound to a solid phase support.

The polymer segment can have any of a number of different geometries, for example, POLY can be linear, branched, or multiarmed. Most typically, POLY is linear or is branched, for example, having 2 polymer arms. Although much of the discussion herein is focused upon PEG as an illustrative POLY, the discussion and structures presented herein can be readily extended to encompass any of the water-soluble polymer segments described above.

Although water-soluble polymers bearing only one or two thiol functionalities are typically used and illustrated herein, polymers bearing two, three, four, five, six, seven, eight, nine, ten, eleven, twelve or more such functionalities can be used. Non-limiting examples of the upper limit of the number of thiol moieties associated with the water-soluble polymer segment include from about 1 to about 500, from 1 to about 100, from about 1 to about 80, from about 1 to about 40, from about 1 to about 20, and from about 1 to about 10.

A preferred type of water soluble polymer, PEG, encompasses poly(ethylene glycol) in any of its linear, branched or multi-arm forms, including end-capped PEG, forked PEG, branched PEG, pendant PEG, and PEG containing one or more degradable linkages separating the monomer subunits, to be more fully described below. The number of repeating ethylene glycol units in a PEG polymer segment typically ranges from about 3 to about 4,000, or from about 12 to about 3,000, or more preferably from about 20 to about 1,000.

Preferred end-capped PEGs are those having as an end-capping moiety such as alkoxy, substituted alkoxy, alkenyloxy, substituted alkenyloxy, alkynyloxy, substituted alkynyloxy, aryloxy, substituted aryloxy. Preferred end-capping groups are $C_1$-$C_{20}$ alkoxy such as methoxy, ethoxy, and benzyloxy. The end-capping group can also advantageously comprise a phospholipid. Exemplary phospholipids include phosphatidylcholines, such as dilauroylphosphatidylcholine, dioleyl phosphatidylcholine, dipalmitoyl phosphatidylcholine, distearoyl phosphatidylcholine, behenoyl phosphatidylcholine, arachidoyl phosphatidylcholine, and lecithin.

A terminus of the polymer which is not thiolated may include, as an alternative to a capping group, a reactive moiety, which is preferably in protected form. Examples of such reactive moieties include hydroxy, amino, ester, carbonate, aldehyde, acetal, aldehyde hydrate, ketone, ketal, ketone hydrate, alkenyl, acrylate, methacrylate, acrylamide, sulfone, carboxylic acid, isocyanate, isothiocyanate, hydrazide, urea, maleimide, vinylsulfone, dithiopyridine, vinylpyridine, iodoacetamide, alkoxy, benzyloxy, silane, lipid, phospholipid, biotin, and fluorescein, including activated and protected forms thereof where applicable. Preferred are functional groups such as N-hydroxysuccinimidyl ester, 1-hydroxybenzotriazolyl carbonate, amine, vinylsulfone, maleimide, N-succinimidyl carbonate, hydrazide, succinimidyl propionate, succinimidyl butanoate, succinimidyl succinate, succinimidyl ester, glycidyl ether, oxycarbonylimidazole, p-nitrophenyl carbonate, aldehyde, orthopyridyldisulfide, and acrylol.

These and other functional groups are described, for example, in the following references, all of which are incorporated by reference herein: N-succinimidyl carbonate (U.S. Pat. Nos. 5,281,698 and 5,468,478), amine (Buckmann et al., *Makromol. Chem.* 182:1379 (1981); Zalipsky et al., *Eur. Polym. J.* 19:1177 (1983)), hydrazide (Andresz et al., *Makromol. Chem.* 179:301 (1978)), succinimidyl propionate and succinimidyl butanoate (Olson et al., in *Poly(ethylene glycol): Chemistry & Biological Applications*, pp. 170-181, Harris & Zalipsky, Eds., ACS, Washington, D.C. (1997); U.S. Pat. No. 5,672,662), succinimidyl succinate (Abuchowski et al., *Cancer Biochem. Biophys.* 7:175 (1984) and Joppich et al., *Makromol. Chem.* 180:1381 (1979)), succinimidyl ester (U.S. Pat. No. 4,670,417), benzotriazole carbonate (U.S. Pat. No. 5,650,234), glycidyl ether (Pitha et al., *Eur. J. Biochem.* 94:11 (1979); Elling et al., *Biotech. Appl. Biochem.* 13:354 (1991)), oxycarbonylimidazole (Beauchamp et al., *Anal. Biochem.* 131:25 (1983); Tondelli et al., *J. Controlled Release* 1:251 (1985)), p-nitrophenyl carbonate (Veronese et al., *Appl. Biochem. Biotech.* 11:141 (1985); Sartore et al., *Appl. Biochem. Biotech.* 27:45 (1991)), aldehyde (Harris et al., *J. Polym. Sci. Chem. Ed.* 22:341 (1984); U.S. Pat. No. 5,824,784; U.S. Pat. No. 5,252,714), maleimide (Goodson et al., *Bio/Technology* 8:343 (1990); Romani et al., in *Chemistry of Peptides and Proteins* 2:29 (1984); Kogan, *Synthetic Comm.* 22:2417 (1992)), orthopyridyl-disulfide (Woghiren et al., *Bioconj. Chem.* 4:314 (1993)), acrylol (Sawhney et al., *Macromolecules* 26:581 (1993)), and vinylsulfone (U.S. Pat. No. 5,900,461).

The POLY types described encompass linear polymer segments as well as branched or multi-arm polymer segments. Examples include PEG molecules having 2 arms, 3 arms, 4 arms, 5 arms, 6 arms, 7 arms, 8 arms or more. Branched polymers used to prepare the thiol polymers of the invention may possess anywhere from 2 to 300 or so reactive termini. Preferred are branched or multi-arm PEGs having 2-8 polymer arms. Branched or multiarm polymers for use in preparing a polymeric thiol of the invention include those represented more generally by the formula $R(POLY)_n$, where R is a central or core molecule from which extends 2 or more POLY arms such as PEG. The variable n represents the number of POLY arms, where each of the polymer arms can independently be end-capped or possess a hydroxyl or other reactive group at its terminus, where at least one polymer arm possesses such a reactive group. Branched PEGs such as those represented generally by the formula, $R(PEG)_n$, above possess at least 2 polymer arms, up to about 300 polymer arms (i.e., n ranges from 2 to about 300). Preferably, such branched PEGs possess from 2 to about 25 polymer arms, more preferably from 2 to about 20 polymer arms, and even more preferably from 2 to about 15 polymer arms or fewer. Most preferred are multi-armed polymers having 3, 4, 5, 6, 7 or 8 arms.

Preferred core molecules in branched PEGs as described above are polyols. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, tetrahydroxyalkanes and the like. Also, ethers of some or all of the former class may serve as core molecules, including dipentaerythritol, tripentaerthritol, hexaglycerol and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

A multi-arm structure corresponding to a polymeric thiol of the invention can be represented by R-(POLY-Y—S—W) x, where POLY, Y, and S—W are as defined above, R represents the core molecule of the multiarm structure, and x is preferably 3 to about 8. Each of the polymer arms can independently be end-capped or possess a thiol group at its terminus, where at least one polymer arm possesses a thiol (or protected thiol) group. Multi-arm PEGs suitable for preparing such structures are available from Nektar Therapeutics (Huntsville, Ala.).

Alternatively, the polymer segment may possess an overall forked structure, e.g., of the type PEG-(Y—S—W)$_2$. This type of polymer segment is useful for reaction with two active agents, where the two active agents are positioned in a precise or predetermined distance apart, depending upon the selection of Y.

Representative PEGs having either linear or branched structures for use in preparing the conjugates of the invention may be purchased from Nektar Therapeutics (Huntsville, Ala.). Illustrative structures are described in Nektar's 2004 catalogue entitled "Polyethylene Glycol and Derivatives for Advanced PEGylation," the contents of which are expressly incorporated herein by reference.

In any of the representative structures provided herein, one or more degradable linkages may be contained in the POLY segment, to allow generation in vivo of a conjugate having a smaller POLY chain than in the initially administered conjugate. Appropriate physiologically cleavable linkages include but are not limited to ester, carbonate ester, carbamate, sulfate, phosphate, acyloxyalkyl ether, acetal, and ketal. Such linkages will preferably be stable upon storage and upon initial administration.

The molecular weight of POLY typically falls in one or more of the following ranges: about 100 to about 100,000 Daltons; about 500 to about 80,000 Daltons; about 1,000 to about 50,000 Daltons; about 2,000 to about 25,000 Daltons; and about 5,000 to about 20,000 Daltons. Exemplary molecular weights include about 1,000, about 5,000, about 10,000, about 15,000, about 20,000, about 25,000, about 30,000, and about 40,000 Daltons. Low molecular weight POLYs possess molecular weights of about 250, 500, 750, 1000, 2000, or 5000 Daltons. Exemplary thiolated polymers comprise PEGs having a molecular weight selected from the group consisting of 5,000, 20,000, and 40,000 Daltons.

In particular embodiments of the invention, a polymeric thiol reagent as provided herein possesses a PEG segment having one of the following molecular weights: 500, 1000, 2000, 3000, 5000, 10,000, 15,000, 20,000, 30,000 and 40,000 Daltons.

In terms of the number of subunits, PEGs for use in the invention will typically comprise a number of (—OCH$_2$CH$_2$—) subunits falling within one or more of the following ranges: from 12 to about 4000 subunits, from about 15 to about 2000 subunits, from about 20 to about 1000 subunits, from about 25 to about 750 subunits, and from about 30 to about 500 subunits.

Preparation of Reagents

One method of preparing "linkerless" polyalkyleneoxy-thiol reagents is shown in Scheme I. In the reaction shown, a polyalkylene glycol having a capping group at one terminus, such as monomethoxy PEG, is alkoxylated with a strong base, such as NaH, and this reagent is combined with a di(haloalkylsulfide) to form a polymeric diether disulfide. This intermediate can then be cleaved with a reducing agent such as dithiothreitol (DTT) to give the polyalkyleneoxy-thiol reagent.

Scheme 1

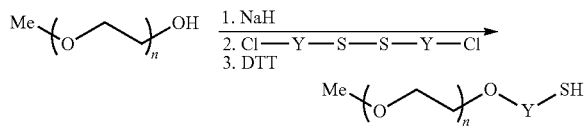

In another synthetic route, shown in Scheme 2, a di(hydroxyalkylsulfide) is used as a core material for polymerization of ethylene oxide, forming a PEG diether disulfide. The termini are capped with, for example, methyl groups. The disulfide can then be cleaved with a reducing agent such as dithiothreitol (DTT) to give the polyalkyleneoxy-thiol reagent.

Scheme 2

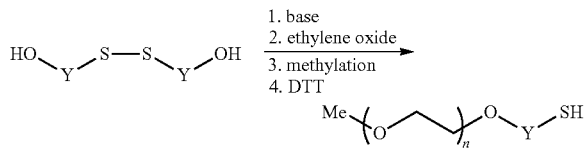

A further strategy is illustrated in Scheme 3. In this route, a reagent POLY-Y—OH, where Y is as defined above, is provided. Such reagents can be prepared, for example, by reaction of a POLY-OH, such as m-PEG-OH, with a strong base such as NaH to form the alkoxide salt, followed by reaction with a haloalkanol, such as 4-bromo-1-butanol. The terminal hydroxy group is converted to a leaving group, such as tosylate or mesylate, and this compound is then reacted with thiourea, displacing the leaving group. The terminal thiouronium salt is then cleaved with base to give the terminal thiol. A variation on this scheme in which the leaving group is a halide is employed in Example 1 below.

Scheme 3

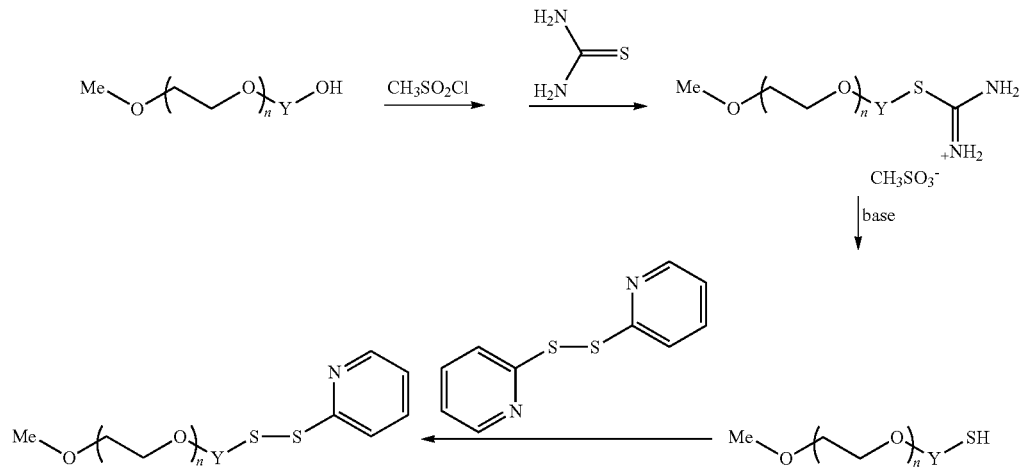

In any of these reagents, the thiol can be protected using a thiol protecting moiety such trityl, thioethers such as alkyl and benzyl thioethers, including monothio, dithio and aminothio acetals, thioesters, thiocarbonates, thiocarbamates, and sulfenyl derivatives. The use of a protecting group during storage further reduces the tendency of the reagents to dimerize. The thiol may also be converted to an ortho-pyridyl disulfide (OPSS), as shown in Scheme 3, which is stable under standard conditions of storage. Under appropriate reaction conditions, the OPSS group reacts smoothly with thiol groups in moieties to be conjugated to the water-soluble polymer, as shown in Example 2.

Preferably, the polymeric reagents of the invention are stored under an inert atmosphere, such as argon or nitrogen. It is also preferable to minimize exposure of the polymers of the invention to moisture. Thus, preferred storage conditions are under dry argon or another dry inert gas at temperatures below about −15° C. Storage under low temperature conditions is preferred, since rates of undesirable side reactions are slowed at lower temperatures. For example, when the polymer segment is PEG, the PEG can react slowly with oxygen to form peroxides, ultimately leading to chain cleavage and increasing the polydispersity of the PEG reagents. In view of the above, it is additionally preferred to store the polymers of the invention in the dark.

Polymer Conjugates

The present invention also encompasses conjugates formed by reaction of any of the herein described polymeric thiol reagents. In general, the polymeric reagents of the invention are useful for conjugation to active agents bearing at least one thiol group available for reaction.

A conjugate of the invention will typically have the structure POLY-[Y—S—S-A]$_x$, where POLY is as defined above, and in preferred embodiments is a polyethylene glycol (PEG); x is 1 to 25, and "A" represents the residue of the active agent following conjugation. In selected embodiments, x is 1 to 8, 1 to 6, or 1 to 4; in further embodiments, x is 1 or x is 2. Y is a divalent linking group having at least four carbon atoms and consisting of a saturated or unsaturated hydrocarbon backbone which is three to ten, preferably three to eight, carbon atoms in length and has substituents which are independently selected from hydrogen, lower alkyl, lower alkenyl, and non-interfering substituents as defined herein, where two such alkyl and/or alkenyl substituents on different carbon atoms of the backbone may be linked so as to form a cycloalkyl, cycloalkenyl, or aryl group.

In selected embodiments, Y has the structure —(CR$^1$R$^2$)n-, where n is 3 to 10, preferably 3 to 8, and each of R$^1$ and R$^2$ is independently selected from hydrogen, lower alkyl, lower alkenyl, and a non-interfering substituent. Two groups R$^1$ and R$^2$ on different carbon atoms may be linked to form a cycloalkyl, cycloalkenyl, or aryl group. The sulfur atom of the thiol (or protected thiol) is attached to an sp$^3$ hybridized carbon atom of Y, rather than to an aryl ring or double bond.

In selected embodiments of Y, Y is C$_3$-C$_8$ alkylene or a combination of C$_3$-C$_8$ alkylene with C$_5$-C$_8$ cycloalkylene or aryl, any of which may include one or more non-interfering substituents, as defined above. Preferably, zero to two, more preferably zero or one, such non-interfering substituents are included.

In further embodiments, Y is a linear or branched alkylene having the formula —(CR$^1$R$^2$)n-, where n is 4 to 8, and each of R$^1$ and R$^2$ is independently selected from hydrogen, lower alkyl, lower alkenyl, and a non-interfering substituent. Preferably, n is 4 to 6, and each of R$^1$ and R$^2$ is independently selected from hydrogen and methyl. In one embodiment, each of R$^1$ and R$^2$ is hydrogen with respect to the n iterations of —(CR$^1$R$^2$)—. In another embodiment, each of R$^1$ and R$^2$ is hydrogen with the exception of R$^1$ on a carbon adjacent said sulfur atom (α-carbon), said R$^1$ being lower alkyl, preferably methyl or ethyl.

In embodiments of Y in which Y is —(CR$^1$R$^2$)n-, where n is 4 to 8, and two groups R$^1$ and R$^2$ on different carbon atoms are linked to form a cycloalkyl, cycloalkenyl, or aryl group, the cycloalkyl group is preferably a cyclopentyl or cyclohexyl group.

In another aspect, a conjugate of the invention can have the structure POLY$_A$-L-SS—Y-POLY$_B$-Y'—SS-A. Each POLY is a water soluble polymer segment, as defined above, where POLY$_B$ is of low molecular weight, e.g. 10 KDa or less, preferably 5 KDa or less, and more preferably 2 KDa or less, and the combined molecular weight of POLY$_A$ and POLY$_B$ is at least 3 KDa. The molecular weight of POLY$_A$ is generally, though not necessarily, of medium to high molecular weight, e.g. greater than about 2 KDa, preferably 5 KDa or greater, and more preferably 10 KDa or greater.

Each of Y and Y' is a spacer group, as defined above for Y, and they may be the same or different. Generally, Y and Y' are identical spacer groups. L is a linker between POLY$_A$ and the adjacent disulfide linkage. Typically, such a linker is a direct bond or a chain of atoms up to about ten atoms in length, containing groups preferably selected from alkyl (C—C), alkenyl, ether, ester, amide, carbamate, and thioester linkages. L may be, but is not necessarily, an embodiment of Y as described herein.

These conjugates are generally the product of a reaction sequence (illustrated in Examples 8-11 below) in which a low molecular weight reagent of the form W—S—S—Y-POLY$_B$-Y'—S—S—W, where S—W is a thiol or, preferably, a thiol-reactive derivative such as OPSS, is first reacted with a biologically active molecule A-SH, e.g. a protein having (or modified to have) a free cysteine residue, to form an intermediate A-S—S—Y-POLY$_B$-Y'—S—S—W. This intermediate is then reacted with a (typically) higher molecular weight reagent of the form POLY$_A$-L-S—S—W to give the final conjugate.

An advantage of such a scheme, particularly for biological molecules with hindered thiol groups, is that a low molecular weight reagent is able to react more efficiently with such a hindered thiol group than would a higher molecular weight reagent. A higher molecular weight polymer can thus be attached to A in greater yield via this scheme than if it were reacted directly with the hindered thiol.

However, if the initial reagent W—S—S—Y-POLY$_B$-Y'—S—S—W lacks the hydrophilic spacer group(s) Y as described herein, the scheme may fail due to low yields in the attachment steps. This difference is illustrated in comparative Examples 9 and 10 below.

In general, the conjugates provided herein are preferably water soluble or dispersible, although the polymeric thiol reagents may also be conjugated to a solid support or surface having active thiol groups.

A thiol group, such as in a cysteine residue, for coupling to an activated polymer of the invention may be naturally occurring (i.e., occurring in the protein or other molecule in its native form), or it may be introduced, e.g. by inserting into the native sequence of a protein in place of a naturally-occurring amino acid, using standard genetic engineering techniques.

When the active agent contains few or only one reactive thiol group(s), the resulting composition may advantageously contain only a single polymer conjugate species. This is useful in conjugation to proteins, which typically have a relatively low number of sulfhydryl groups (as compared to other active groups such as amines) accessible for conjugation.

Covalent attachment via thiol groups can thus result in more selective modification of the target protein. Accordingly, the use of polymeric thiols can allow greater control over the resulting polymer conjugate, both in the number of polymer derivatives attached to the parent protein and the position of polymer attachment.

Candidate Molecules for Conjugation

A biologically active agent for use in preparing a conjugate of the invention may fall into one of a number of structural classes, including but not limited to peptides, polypeptides, proteins, antibodies, polysaccharides, steroids, nucleotides, oligonucleotides, polynucleotides, fats, electrolytes, small molecules (preferably insoluble small molecules), and the like. Preferably, an active agent for coupling to a polymer of the invention possesses a native sulfhydryl group or is modified to contain at least one reactive sulfhydryl group suitable for coupling.

Preferred peptides or proteins for coupling to a polymeric thiol of the invention include EPO, IFN-α, IFN-β, IFN-γ, consensus IFN, Factor VII, Factor VIII, Factor IX, IL-2, Remicade™ (infliximab), Rituxan™ (rituximab), Enbrel™ (etanercept), Synagis™ (palivizumab), Reopro™ (abciximab), Herceptin™ (trastuzimab), tPA, Cerizyme™ (imiglucerase), hepatitis-B vaccine, rDNAse, alpha-1 proteinase inhibitor, G-CSF, GM-CSF, hGH, insulin, FSH, and PTH. In selected embodiments, the protein is G-CSF or GM-CSF.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted (e.g., cysteine), deleted, or the like, as long as the resulting variant protein possesses at least a certain degree of activity of the parent (native) protein.

Suitable agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) anti-arthritics, antimalarials, antiemetics, anepileptics, bronchodilators, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Other specific examples of active agents include but are not limited to asparaginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922, 675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Methods of Conjugation

Suitable conjugation conditions are those conditions of time, temperature, pH, reagent concentration, solvent, and the like sufficient to effect conjugation between a polymeric thiol reagent and an active agent. As is known in the art, the specific conditions depend upon, among other things, the active agent, the type of conjugation desired, the presence of other materials in the reaction mixture, and so forth. Sufficient conditions for effecting conjugation in any particular case can be determined by one of ordinary skill in the art upon a reading of the disclosure herein, reference to the relevant literature, and/or through routine experimentation.

Exemplary conjugation conditions include carrying out the conjugation reaction at a pH of from about 6 to about 10, and at, for example, a pH of about 6.0, 6.5, 7.0, 7.5, 8.0, 8.5, 9.0, 9.5, or 10. The reaction is allowed to proceed from about 5 minutes to about 72 hours, preferably from about 30 minutes to about 48 hours, and more preferably from about 4 hours to about 24 hours or less. Temperatures for conjugation reactions are typically, although not necessarily, in the range of from about 0° C. to about 40° C.; conjugation is often carried out at room temperature or less. Conjugation reactions are often carried out in a buffer such as a phosphate or acetate buffer or similar system.

With respect to reagent concentration, an excess of the polymeric reagent is typically combined with the active agent. In some cases, however, it is preferred to have stoichiometric amounts of the number of reactive groups on the polymeric reagent to the amount of active agent. Exemplary ratios of polymeric reagent to active agent include molar ratios of about 1:1 (polymeric reagent:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

More preferably, a polymeric thiol of the invention is typically conjugated to a sulfhydryl-containing active agent at a pH of about 6-9 (e.g., at 6, 6.5, 7, 7.5, 8, 8.5, or 9), more preferably at a pH of about 7-9, and even more preferably at a pH of about 7 to 8. Generally, a slight molar excess of polymeric reagent is employed, for example, a 1.5 to 15-fold molar excess, preferably a 2-fold to 10 fold molar excess. Reaction times generally range from about 15 minutes to several hours, e.g., 8 or more hours, at room temperature. For sterically hindered sulfhydryl groups, required reaction times may be significantly longer.

Purification of Conjugates

Optionally, conjugates produced by reacting a polymeric thiol of the invention with a biologically active agent are purified to obtain/isolate different species, e.g., PEG-species, or to remove undesirable reaction side-products.

If desired, PEG conjugates having different molecular weights can be isolated using gel filtration chromatography. While this approach can be used to separate PEG conjugates having different molecular weights, this approach is generally ineffective for separating positional isomers having different PEGylation sites within a protein. For example, gel filtration chromatography can be used to separate from each other mixtures of PEG 1-mers, 2-mers, 3-mers, etc., although each of the recovered PEG-mer compositions may contain PEGs attached to different reactive groups within the protein.

Gel filtration columns suitable for carrying out this type of separation include Superdex™ and Sephadex™ columns available from Amersham Biosciences. Selection of a particular column will depend upon the desired fractionation range desired. Elution is generally carried out using a non-amine based buffer, such as phosphate, acetate, or the like. The collected fractions may be analyzed by a number of different methods, for example, (i) OD at 280 nm for protein content, (ii) BSA protein analysis, (iii) iodine testing for PEG content (Sims, G. E. C. et al., *Anal. Biochem*, 107, 60-63, 1980), or alternatively, (iv) by running an SDS PAGE gel, followed by staining with barium iodide.

Separation of positional isomers can be carried out by reverse phase chromatography using, for example, an RP-HPLC C18 column (Amersham Biosciences or Vydac) or by ion exchange chromatography using an ion exchange column, e.g., a Sepharose™ ion exchange column available from Amersham Biosciences. Either approach can be used to separate PEG-biomolecule isomers having the same molecular weight (positional isomers).

Depending upon the intended use for the resulting PEG-conjugates, following conjugation, and optionally additional separation steps, the conjugate mixture may be concentrated, sterile filtered, and stored at low temperatures from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized protein conjugate powder formulation is absent residual buffer. Alternatively, a buffer exchange step may be used using a formulation buffer, so that the lyophilized conjugate is in a form suitable for reconstitution into a formulation buffer and ultimately for administration to a mammal.

Pharmaceutical Compositions

The present invention also includes pharmaceutical preparations comprising a conjugate as provided herein in combination with a pharmaceutical excipient. Generally, the conjugate itself will be in a solid form (e.g., a precipitate or a lyphilizate) or in solution, which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

Methods of Administration

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

Cleavage of the water-soluble polymer portion of the conjugate in vivo, when desired, can be effected through the use of physiologically cleavable and/or enzymatically degradable linkages, such as urethane, amide, carbonate or ester-containing linkages, in the polymer backbone. In this way, clearance of the conjugate (via cleavage of water-soluble polymer portions) can be modulated by selecting the polymer molecular size and the type functional group that would provide the desired clearance properties. One of ordinary skill in the art can determine the proper molecular size of the polymer as well as the cleavable linkages. For example, one of ordinary skill in the art, using routine experimentation, can determine a proper molecular size and cleavable functional group by first preparing a variety of polymer derivatives with different polymer weights and cleavable linkages, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

All articles, books, patents, patent publications and other publications referenced herein are incorporated by reference in their entireties.

EXAMPLES

The following examples illustrate but in no way are intended to limit the scope of the present invention. In one aspect, the Examples illustrate the increased stability, during synthesis and conjugation, of the polymeric thiol reagents of the invention.

$^1$H NMR data was obtained using a 400 MHz spectrometer manufactured by Bruker.

PEG reagents referred to are available from Nektar Therapeutics, Huntsville, Ala.

Example 1

Preparation of mPEG-$(CH_2)_4$-orthopyridyl disulfide (mPEG-4C-OPSS)

I. mPEG$_{5000}$-butyl bromide

A solution of mPEG$_{5000}$ (20.0 g, 0.004 mol) (NOF Corporation) in toluene (200 ml) was azeotropically dried by distilling off 50 ml toluene. Sodium hydride (0.8 g, 60% dispersion in mineral oil, 0.020 mol) was added, and the mixture was stirred for 1 h at 60° C. under an argon atmosphere. 1,4-Dibromobutane (9.0 g, 0.0417 mol) was added, and the mixture was stirred overnight at 75° C. under argon. The mixture was filtered and concentrated under reduced pressure, and the residue was combined with 850 ml cold ethyl ether. The precipitated product was filtered off and dried under reduced pressure. Yield 17.4 g. NMR ($d_6$-DMSO): 1.60 ppm (m, —O—$CH_2$—$CH_2$—$CH_2$—$CH_2$—Br, 2H), 1.84 ppm (m, —O—$CH_2$—$\overline{CH_2}$—$CH_2$—$CH_2$—Br, 2H), 3.24 ppm (s, —$OCH_3$, 3H), 3.51 ppm (s, PEG backbone).

II. mPEG$_{5000}$-butanethiol

To a solution of mPEG$_{5000}$-butyl bromide (2.0 g, 0.0004 mol) in anhydrous ethyl alcohol (20 ml), thiourea (0.31 g, 0.0041 mol) was added, and the mixture was stirred overnight at 78° C. under argon. The solvent was removed by distillation under reduced pressure, and the residue was dissolved in 1% aqueous NaOH (21 ml). This solution was heated for 2.5 h at 85° C. under argon. After cooling the solution to 35° C., the pH was adjusted to 3 with 10% phosphoric acid. NaCl (6 g) was added, and the product was extracted with dichloromethane. The extract was dried with anhydrous sodium sulfate, and the product was precipitated with cold ethyl ether. Yield 1.8 g. NMR ($CDCl_3$): 1.35 ppm (t, —$CH_2$—$\underline{SH}$, 1H), 1.69 ppm (m, —O—$CH_2$—$CH_2$—$CH_2$—$CH_2$—SH, 4H), 2.55 ppm (m, —$\underline{CH_2}$—SH, 2H), 2.69 ppm (t, —$CH_2$—S—S—$CH_2$—, $\overline{4H}$, 1.2 mol %) 3.24 ppm (s, —$OCH_3$, 3H), 3.51 ppm (s, PEG backbone).

Iodometric analysis showed that the product contained 94% thiol groups. The NMR data, above, indicated that the product contained a very small amount (1.2 mol % by NMR) of disulfide-linked dimer, formed by oxidation of thiol groups. No further purification of the thiol was required.

In contrast, the analogous preparation of mPEG$_{5000}$-ethanethiol (i.e. the corresponding reagent containing only a two-carbon spacer between the PEG and the thiol group) from mPEG$_{5000}$-mesylate and thiourea, conducted in a similar manner, produced product containing about 15 mol % of disulfide-linked dimer containing dithiol group (see e.g. WO 2004/063250). This level of dimer necessitates further purification or additional chemical treatment to convert the dimer to the desired PEG-thiol.)

III. mPEG$_{5000}$-4C-OPSS

To a solution of mPEG$_{5000}$-butanethiol (2.0 g, 0.0004 mol) in anhydrous methyl alcohol (40 ml), 2,2'-dipyridyl disulfide (0.18 g, 0.00082 mol) was added, and the mixture was stirred for 4 h at room temperature under argon. The solvent was removed by distillation under reduced pressure, the residue was dissolved in dichloromethane (5 ml), and the product was precipitated with 50 ml of cold ethyl ether. Yield 1.7 g. NMR (CDCl$_3$): 1.68 ppm (m, —O—CH$_2$—CH$_2$—CH$_2$—CH$_2$—S—, 2H), 1.76 ppm (m, —O—CH$_2$—CH$_2$—CH$_2$—CH$_2$—S—, 2H), 2.82 ppm (t, —CH$_2$—S—, 2H), 3.38 ppm (s, —OCH$_3$, 3H), 3.52 ppm (s, PEG backbone), 7.12, 7.68, 7.75, & 8.47 ppm (4 m, pyridyl protons, 4H).

Example 2

Preparation of PEG$_{2000}$-di-((CH$_2$)$_4$-orthopyridyl disulfide) (PEG-di-(4C-OPSS), 2 KDa)

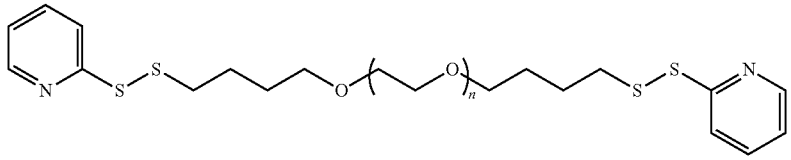

PEG$_{2000}$-di-butyl bromide

A solution of PEG$_{2000}$ (20.0 g, 0.020 equiv.) (NOF Corporation) in toluene (150 ml) was azeotropically dried by distilling off 50 ml toluene. Sodium hydride (6.0 g, 60% dispersion in mineral oil, 0.150 mol) was added, and the mixture was stirred for 1 h at 60° C. under an argon atmosphere. 1,4-Dibromobutane (34.55 g, 1.600 mol) was added, and the mixture was stirred overnight at 75° C. under argon. The mixture was filtered and concentrated under reduced pressure, and the residue was combined with 850 ml cold ethyl ether. The precipitated product was filtered off and dried under reduced pressure. Yield 17.0 g. NMR (d$_6$-DMSO): 1.60 ppm (m, —O—CH$_2$—CH$_2$—CH$_2$—CH$_2$—Br, 2H), 1.84 ppm (m, —O—CH$_2$—CH$_2$—CH$_2$—CH$_2$—Br, 2H), 3.51 ppm (s, PEG backbone); substitution 96.3%.

PEG$_{2000}$-di(butanethiol)

To a solution of PEG$_{2000}$-di(butyl bromide) (10.0 g, 0.0100 equiv.) in anhydrous ethyl alcohol (100 ml), thiourea (7.68 g, 99%, 0.100 mol) was added, and the mixture was stirred overnight at 78° C. under argon. The solvent was removed by distillation under reduced pressure, and the residue was dissolved in 3.3% aqueous NaOH (180 ml). This solution was heated for 2.5 h at 85° C. under argon. After cooling the solution to 35° C., 60 ml deionized water was added, and the pH was adjusted to 3 with 10% phosphoric acid. The solution was washed with 50 ml ethyl acetate, and the product was extracted with dichloromethane. The extract was dried with anhydrous sodium sulfate and the solvent was removed by distillation under reduced pressure. The crude product was recrystallised from isopropyl alcohol and dried under vacuum. Yield 7.8 g. NMR (CDCl$_3$): 1.35 ppm (t, —CH$_2$—SH, 1H), 1.69 ppm (m, —O—CH$_2$—CH$_2$—CH$_2$—CH$_2$—SH, 4H), 2.55 ppm (m, —CH$_2$—SH, 2H), 2.69 ppm (t, —CH—S—S—CH$_2$—, 4H, 1.9 mol %), 3.64 ppm (s, PEG backbone).

The NMR data, above, indicated that the product contained a relatively small amount (1.9 mol % by NMR) of disulfide-linked dimer, formed by oxidation of thiol groups. No further purification of the thiol was required.

In contrast, the analogous preparation of PEG$_{2000}$-diethanethiol (i.e. the corresponding reagent containing only a two-carbon spacer between the PEG and the thiol group) from PEG$_{2000}$-di-mesylate and thiourea, conducted in a similar manner, produced product containing about 41 mol % of disulfide-linked dimer containing dithiol group.

PEG$_{2000}$-di-(4C-OPSS)

To a solution of 2,2'-dipyridyl disulfide (0.89 g, 0.0040 mol) in anhydrous methyl alcohol (40 ml), PEG$_{2000}$-di-butanethiol (2.0 g, 0.0020 equiv.) was added, and the mixture was stirred for 3 h at room temperature under argon. The solvent was removed by distillation under reduced pressure, the residue was dissolved in dichloromethane (5 ml), and the product was precipitated with 50 ml of cold ethyl ether. The precipitation was repeated giving 1.0 g of white solid product. NMR (CDCl$_3$): 1.68 ppm (m, —O—CH$_2$—CH$_2$—CH$_2$—CH$_2$—S—, 2H), 1.76 ppm (m, —O—CH$_2$—CH$_2$—CH$_2$—CH$_2$—S—, 2H), 2.82 ppm (t, —CH$_2$—S—, 2H), 3.64 ppm (s, PEG backbone), 7.12, 7.68, 7.75, & 8.47 ppm (4 m, pyridyl Hs, 4H).

Example 3

Preparation of mPEG$_{10,000}$-(CH$_2$)$_4$-orthopyridyl disulfide (mPEG-4C-OPSS, 10 KDa)

mPEG$_{10,000}$-butyl bromide

A solution of mPEG$_{10,000}$ (20.0 g, 0.002 mol) (NOF Corporation) in toluene (200 ml) was azeotropically dried by distilling off 50 ml toluene. Sodium hydride (0.8 g, 60% dispersion in mineral oil, 0.0200 mol) was added, and the mixture was stirred for 1 h at 60° C. under an argon atmosphere. 1,4-Dibromobutane (4.8 g, 0.0222 mol) was added, and the mixture was stirred overnight at 75° C. under argon. The mixture was filtered and concentrated under reduced pressure, and the residue was combined with 850 ml cold ethyl ether. The precipitated product was filtered off and dried under reduced pressure. Yield 18.5 g. NMR (d$_6$-DMSO): 1.60 ppm (m, —O—CH$_2$—CH$_2$—CH$_2$—CH$_2$—Br, 2H), 1.84 ppm (m, —O—CH$_2$—CH$_2$—CH$_2$—CH$_2$—Br, 2H), 3.24 ppm (s, —OCH$_3$, 3H), 3.51 ppm (s, PEG backbone); substitution 97.5%.

mPEG$_{10,000}$-butanethiol

To a solution of mPEG$_{10,000}$-butyl bromide (10.0 g, 0.0010 mol) in anhydrous ethyl alcohol (100 ml), thiourea (0.77 g, 99%, 0.0100 mol) was added, and the mixture was stirred overnight at 78° C. under argon. The solvent was removed by distillation under reduced pressure, and the residue was dissolved in 1.0% aqueous NaOH (90 ml). This solution was heated for 3 h at 85° C. under argon. After cooling the solution to room temperature NaCl (10 g) was added and the pH was adjusted to 3 with 10% phosphoric acid. The product was extracted with dichloromethane. The extract was dried with anhydrous sodium sulfate, and the solvent was removed by distillation under reduced pressure. The crude product was dissolved in small amount of dichloromethane, precipitated with ethyl ether and dried under vacuum. Yield 9.0 g. NMR (CDCl$_3$): 1.35 ppm (t, —CH$_2$—SH, 1H), 1.69 ppm (m, —O—CH$_2$—CH$_2$—CH$_2$—CH$_2$—SH, 4H), 2.55 ppm (m, —CH$_2$—SH, 2H), 2.69 ppm (t, —CH$_2$—S—S—CH$_2$—, 4H, 4.8 mol %), 3.38 ppm (s, —OCH$_3$, 3H), 3.64 ppm (s, PEG backbone). The NMR data, above, indicated that the product contained a relatively small amount (4.8 mol % by NMR) of disulfide-linked dimer, formed by oxidation of thiol groups. No further purification of the thiol was required.

mPEG$_{10,000}$-4C-OPSS

To a solution of 2,2'-dipyridyl disulfide (0.10 g, 0.00045 mol) in anhydrous methyl alcohol (40 ml), mPEG$_{10,000}$-butanethiol (2.0 g, 0.00020 equiv.) was added, and the mixture was stirred for 3 h at room temperature under argon. The solvent was removed by distillation under reduced pressure. The crude product was dissolved in dichloromethane (5 ml) and precipitated with 50 ml of cold ethyl ether giving after drying 1.8 g of white solid powder. NMR (CDCl$_3$): 1.68 ppm (m, —O—CH$_2$—CH$_2$—CH$_2$—CH$_2$—S—, 2H), 1.76 ppm (m, —O—CH$_2$—CH$_2$—CH$_2$—CH$_2$—S—, 2H), 2.82 ppm (t, —CH$_2$—S—, 2H), 3.38 ppm (s, —OCH$_3$, 3H), 3.64 ppm (s, PEG backbone), 7.12, 7.68, 7.75, & 8.47 ppm (4 m, pyridyl protons, 4H).

Examples 4 and 5 illustrate the preparation of corresponding reagents of higher molecular weight.

Example 4

Preparation of mPEG$_{20,000}$-(CH$_2$)$_4$-orthopyridyl disulfide (mPEG-4C-OPSS, 20 KDa)

mPEG$_{20,000}$-butyl bromide

A solution of mPEG$_{20,000}$ (20.0 g, 0.0010 mol) (NOF Corporation) in toluene (200 ml) was azeotropically dried by distilling off 50 ml toluene. Sodium hydride (0.4 g, 60% dispersion in mineral oil, 0.0100 mol) was added, and the mixture was stirred for 1 h at 60° C. under an argon atmosphere. 1,4-Dibromobutane (2.4 g, 0.0111 mol) was added, and the mixture was stirred overnight at 75° C. under argon. The mixture was filtered and concentrated under reduced pressure, and the residue was combined with 850 ml cold ethyl ether. The precipitated product was filtered off and dried under reduced pressure. Yield 18.2 g. NMR (d$_6$-DMSO): 1.60 ppm (m, —O—CH$_2$—CH$_2$—CH$_2$—CH$_2$—Br, 2H), 1.84 ppm (m, —O—CH$_2$—CH$_2$—CH$_2$—CH$_2$—Br, 2H), 3.24 ppm (s, —OCH$_3$, 3H), 3.51 ppm (s, PEG backbone); substitution 98.0%.

mPEG$_{20,000}$-butanethiol

To a solution of mPEG$_{20,000}$-butyl bromide (10.0 g, 0.5 mmol) in anhydrous ethyl alcohol (100 ml), thiourea (0.39 g, 99%, 0.0051 mol) was added, and the mixture was stirred overnight at 78° C. under argon. The solvent was removed by distillation under reduced pressure, and the residue was dissolved in 1.0% aqueous NaOH (90 ml). This solution was heated for 3 h at 85° C. under argon. After cooling the solution to room temperature NaCl (10 g) was added, and the pH was adjusted to 3 with 10% phosphoric acid. The product was extracted with dichloromethane. The extract was dried with anhydrous sodium sulfate, and the solvent was removed by distillation under reduced pressure. The crude product was dissolved in a small amount of dichloromethane, precipitated with ethyl ether and dried under vacuum. Yield 8.2 g. NMR (CDCl$_3$): 1.35 ppm (t, —CH$_2$—SH, 1H), 1.69 ppm (m, —O—CH$_2$—CH$_2$—CH$_2$—CH$_2$—SH, 4H), 2.55 ppm (m, —CH$_2$—SH, 2H), 2.69 ppm (t, —CH$_2$—S—S—CH$_2$—, 4H, 3.4 mol %), 3.38 ppm (s, —OCH$_3$, 3H), 3.64 ppm (s, PEG backbone). The NMR data, above, indicated that the product contained a relatively small amount (3.4 mol % by NMR) of disulfide-linked dimer, formed by oxidation of thiol groups. No further purification of the thiol was required.

mPEG$_{20,000}$-4C-OPSS

To a solution of 2,2'-dipyridyl disulfide (0.05 g, 0.00023 mol) in anhydrous methyl alcohol (40 ml), mPEG$_{20,000}$-butanethiol (2.0 g, 0.00010 mol) was added, and the mixture was stirred for 3 h at room temperature under argon. The solvent was removed by distillation under reduced pressure, the residue was dissolved in dichloromethane (5 ml), and the product was precipitated with 50 ml ethyl ether giving 1.9 g of white solid powder. NMR (CDCl$_3$): 1.68 ppm (m, —O—CH$_2$—CH$_2$—CH$_2$—CH$_2$—S—, 2H), 1.76 ppm (m, —O—CH$_2$—CH$_2$—CH$_2$—CH$_2$—S—, 2H), 2.82 ppm (t, —CH$_2$—S—, 2H), 3.38 ppm (s, —OCH$_3$, 3H), 3.64 ppm (s, PEG backbone), 7.12, 7.68, 7.75, & 8.47 ppm (4 m, pyridyl protons, 4H).

Example 5

Preparation of PEG$_{30,000}$-(CH$_2$)$_4$-orthopyridyl disulfide (mPEG-4C-OPSS, 30 KDa)

mPEG$_{30,000}$-butyl bromide

A solution of mPEG$_{30,000}$ (20.0 g, 0.00067 mol) (NOF Corporation) in toluene (150 ml) was azeotropically dried by distilling off 50 ml toluene. Sodium hydride (0.3 g, 60% dispersion in mineral oil, 0.00750 mol) was added, and the mixture was stirred for 1 h at 60° C. under an argon atmosphere. 1,4-Dibromobutane (2.17 g, 0.0100 mol) was added, and the mixture was stirred overnight at 75° C. under argon. The mixture was filtered and concentrated under reduced pressure, and the residue was combined with 850 ml cold ethyl ether. The precipitated product was filtered off and dried under reduced pressure. Yield 15.3 g. NMR (d$_6$-DMSO): 1.60 ppm (m, —O—CH$_2$—CH$_2$—CH$_2$—CH$_2$—Br, 2H), 1.84 ppm (m, —O—CH$_2$—CH$_2$—CH$_2$—CH$_2$—Br, 2H), 3.24 ppm (s, —OCH$_3$, 3H), 3.51 ppm (s, PEG backbone); substitution 96.0%.

mPEG$_{30,000}$-butanethiol

To a solution of mPEG$_{30,000}$-butyl bromide (10.0 g, 0.00033 mol) in anhydrous ethyl alcohol (100 ml), thiourea (0.26 g, 99%, 0.00338 mol) was added, and the mixture was stirred overnight at 78° C. under argon. The solvent was removed by distillation under reduced pressure, and the residue was dissolved in 1.0% aqueous NaOH (90 ml). This solution was heated for 2.5 h at 85° C. under argon. After cooling to room temperature NaCl (10 g) was added and the pH was adjusted to 3 with 10% phosphoric acid. The product was extracted with dichloromethane. The extract was dried with anhydrous sodium sulfate and the solvent was removed by distillation under reduced pressure. The crude product was dissolved in a small amount of dichloromethane, precipitated with ethyl ether and dried under vacuum. Yield 9.4 g. NMR (CDCl$_3$): 1.35 ppm (t, —CH$_2$—SH, 1H), 1.69 ppm (m, —O—CH$_2$—CH$_2$—CH$_2$—CH$_2$—SH, 4H), 2.55 ppm (m, —CH$_2$—SH, 2H), 2.69 ppm (t, —CH$_2$—S—S—CH$_2$—, 4H, 3.8 mol %), 3.38 ppm (s, —OCH$_3$, 3H), 3.64 ppm (s, PEG backbone). The NMR data, above, indicated that the product contained a relatively small amount (3.8 mol % by NMR) of disulfide-linked dimer, formed by oxidation of thiol groups. No further purification of the thiol was required.

mPEG$_{30,000}$-4C-OPSS

To a solution of 2,2'-dipyridyl disulfide (0.05 g, 0.00023 mol) in anhydrous methyl alcohol (60 ml), mPEG$_{30,000}$-butanethiol (3.0 g, 0.00010 mol) was added, and the mixture was stirred for 3 h at room temperature under argon. The solvent was removed by distillation under reduced pressure, the residue was dissolved in dichloromethane (8 ml), and the product was precipitated with 60 ml ethyl ether giving 2.9 g of white solid powder. NMR (CDCl$_3$): 1.68 ppm (m, —O—CH$_2$—CH$_2$—CH$_2$—CH$_2$—S—, 2H), 1.76 ppm (m, —O—CH$_2$—CH$_2$—CH$_2$—CH$_2$—S—, 2H), 2.82 ppm (t, —CH$_2$—S—, 2H), 3.38 ppm (s, —OCH$_3$, 3H), 3.64 ppm (s, PEG backbone), 7.12, 7.68, 7.75, & 8.47 ppm (4 m, pyridyl protons, 4H).

Example 6

Conjugation of BSA with mPEG$_{5000}$-4C-OPSS and with mPEG$_{5000}$-MAL (MAL=maleimide) (Comparative)

Reduction of BSA (Cleavage of Disulfide Linkages)

A 3.1 mg sample of BSA was added to a 5 mL ReactiVial™ containing 3.1 mL 1×PBS pH 7.5. The solution was placed on a stir plate at medium speed. A 4.62 mg sample of dithiothreitol (DTT) was added to the solution with stirring and allowed to react for 2 hrs at room temperature, reducing the sample completely.

The reaction mixture was placed in a 350 mL Amicon StirCell with a 10,000 MW PES membrane for removal of DTT. Buffer (1×PBS pH 7.5) was added to a volume of 350 mL, with stirring to prevent settling. Pressure was applied to the apparatus (60 psi) until the volume was reduced to <10 mL. PBS was again added to a volume of 350 mL, and the process was repeated twice. A 1 mL aliquot was frozen for standards (gels, HPLC, etc.), and the remaining volume was used in the conjugation step.

Conjugation

Reduced BSA from step A (4 mL) was combined with 2.35 mg (10× excess) mPEG$_{5K}$-4C-OPSS, described in Example 1, in a 5 mL ReactiVial on a stir plate set to the medium setting. A similar reaction mixture was prepared using reduced BSA from step A (4 mL) and 2.35 mg (10× excess) mPEG$_{5K}$-MAL. (In mPEG-MAL, available from Nektar Therapeutics, Huntsville, Ala., maleimide is attached via the ring nitrogen to the terminal —OCH$_2$CH$_2$— of mPEG.) The vials were left at room temperature for 60 hrs.

Analysis

The reaction mixtures were run on 10% Bis-Tris NuPAGE Gels (Invitrogen) using the following conditions.

| | |
|---|---|
| 4× LDS Sample Buffer (Invitrogen) | 10 µL/sample |
| Reaction Sample | 30 µL/sample |
| 1× MES Running Buffer (Invitrogen) | 600 mL |
| MultiMark Protein Standards (Invitrogen) | 7 µL |
| SimplyBlue Safe Stain (Invitrogen) | 50 mL |
| Loading Sample (a + b) | 30 µL |
| Voltage | 200 V |
| Amps | 400 mA |
| Time | 36 min. |

Figure 2:
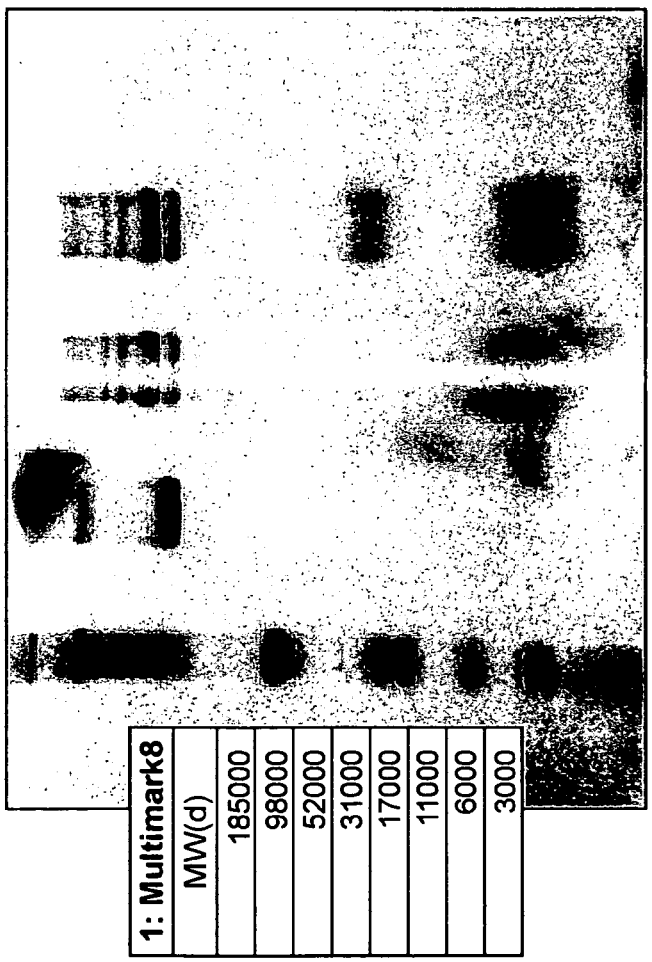
FIG. 2 shows the gel of FIG. 1 additionally stained with Barium Iodine, for detection of PEG.

FIG. 1 shows the finished gel stained with SimplyBlue Safe Stain. FIG. 2 shows the same gel additionally stained with Barium Iodine, for detecting PEG.

The molecular weight and relative intensity of the species shown in the gel of FIG. 2 are also set forth in the table below:

| Lane 2: Reduced BSA | | Lane 3: PEG$_{5K}$-MAL conjugation reaction | | Lane 4: PEG$_{5K}$-OPSS conjugation reaction | |
|---|---|---|---|---|---|
| MW | Rel. Int. | MW | Rel. Int. | MW | Rel. Int. |
| 100718.7 | 0.0727 | 126546.9 | 0.0591 | 134703.1 | 0.0433 |
| 50521.2 | 0.9273 | 85120 | 0.0852 | 85120 | 0.0664 |
| | | 75000 | 0.1449 | 75460 | 0.0826 |
| | | 58440 | 0.3984 | 58440 | 0.4224 |
| | | 50077.5 | 0.1822 | 50077.5 | 0.2032 |
| | | 7883.1$^a$ | 0.1301 | 22090.9$^a$ | 0.0806 |
| | | | | 6454.5$^a$ | 0.1015 |

$^a$visualized by BaI (for detection of PEG)

The PEG$_{5K}$-MAL-BSA conjugation reaction yielded 39.8% mono PEGmers (58440 MW bands), and the mPEG$_{5K}$-4C-OPSS-BSA conjugation reaction yielded 42.2% mono PEGmers. Accordingly, the conjugation behavior of the polymeric thiol reagent of the invention was better than that observed for a reference polymeric reagent (maleimide-terminated polymer), indicating that significant dimerization of PEG-OPSS, which is typical for the corresponding reagent based on mPEG-ethanethiol, did not occur.

Example 7

PEGylation of Granulocyte-Colony Stimulating Factor (G-CSF) with mPEG$_{10,000}$-(CH$_2$)$_4$-orthopyridyl disulfide (mPEG$_{10,000}$-4C-OPSS)

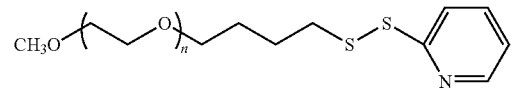

mPEG$_{10,000}$-(CH$_2$)$_4$-orthopyridyl disulfide
(mPEG$_{10,000}$-4C-OPSS)

A fifty-fold excess (relative to the amount of G-CSF in a measured aliquot of stock G-CSF solution) of mPEG$_{10,000}$-(CH$_2$)$_4$-orthopyridyl disulfide (mPEG$_{10,000}$-4C-OPSS), as prepared in Example 3, was dissolved in dimethylsulfoxide (DMSO) to form a 10% reagent solution. The 10% reagent solution was quickly added to the aliquot of stock G-CSF solution (0.4 mg/ml in sodium phosphate buffer, pH 7.0) and mixed well. To allow for coupling of the mPEG-OPSS reagent to the free (i.e., nonintraprotein-disulfide bond participating) cysteine residue at position 17 of G-CSF, the reaction solution was placed on a RotoMix (Type 48200, Thermolyne, Dubuque Iowa) to facilitate conjugation at 37° C. After thirty minutes, another fifty-fold excess of mPEG$_{10,000}$-4C-OPSS was added to the reaction solution, followed by mixing first for thirty minutes at 37° C., and then for two hours at room temperature, to thereby form an mPEG$_{10,000}$-G-CSF conjugate solution.

The mPEG$_{10,000}$-G-CSF conjugate solution was characterized by SDS-PAGE and RP-HPLC. The PEGylation reaction was determined to yield 36% of mPEG$_{10,000}$-G-CSF conjugate (a monoPEGylated conjugate at a cysteine residue of G-CSF). Cation-exchange chromatography was used to purify the conjugate.

The same approach can be used to prepare other conjugates using mPEG-4C-OPSS reagents having other molecular weights.

Examples 8-10, following, employ an approach (illustrated schematically below) in which a polymeric reagent having a relatively low molecular weight (PEG$_B$ in the schematic) is initially attached to a moiety to be conjugated (A), followed by attachment of a higher molecular weight polymeric reagent (PEG$_A$ in the schematic) to the polymeric portion of the conjugate formed from attachment of the low molecular weight reagent to the conjugated moiety. Using this approach, it is possible to efficiently modify a hindered site. In the Examples below, the hindered site is the partially buried free thiol-containing cysteine residue of G-CSF.

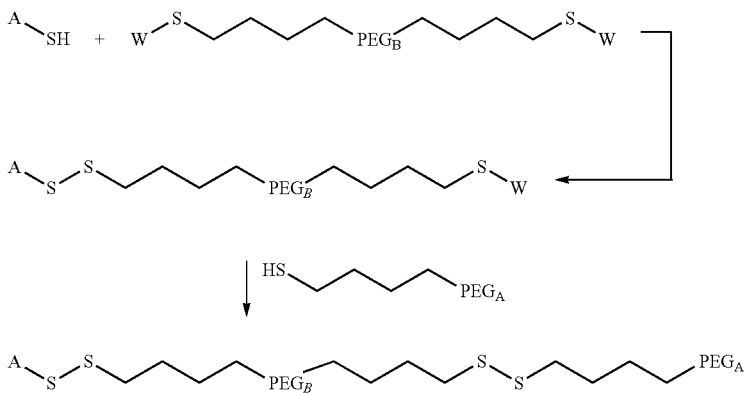

Example 8a

PEGylation of G-CSF with PEG$_{2000}$-di-(C$_2$)$_4$-orthopyridyl disulfide and mPEG$_{2000}$-butanethiol

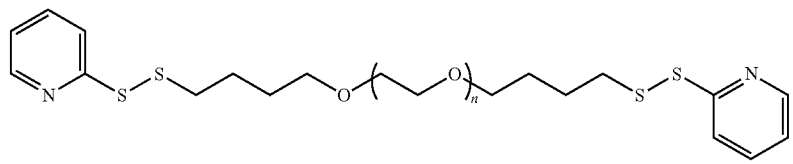

PEG$_{2000}$-di-((CH$_2$)$_4$-orthopyridyl disulfide)
(PEG$_{2,000}$-di-(4C-OPSS)

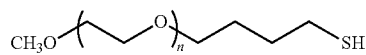

mPEG$_{20,000}$-butanethiol
(mPEG$_{20K}$-4C-SH)

In this Example, the bifunctional PEG-di-(4C-OPSS) reagent is inserted into the sterically hindered free thiol via a disulfide linkage, followed by the coupling of mPEG$_{20K}$-butanethiol to the free residue of the PEG$_{2,000}$-di-(4C-OPSS) reagent, via a further disulfide linkage.

PEG$_{2,000}$-di-(4C-OPSS), as prepared in Example 2, stored at $-20°$ C. under argon, was warmed to ambient temperature. A fifty-fold excess (relative to the amount of G-CSF in a measured aliquot of stock G-CSF solution) of the reagent was dissolved in DMSO to form a 10% solution. The 10% reagent solution was quickly added to the aliquot of stock G-CSF solution (0.4 mg/ml in sodium phosphate buffer, pH 7.0) and mixed well. The reaction solution was placed on a RotoMix (Type 48200, Thermolyne, Dubuque Iowa), and was allowed to mix for one hour at 37° C., and then for two hours at room temperature. After the reaction was complete, the reaction solution was dialyzed against sodium phosphate buffer, pH 7.0, to remove excess free PEG$_{2,000}$-di-(4C-OPSS).

A fifty-fold excess (relative to G-CSF) of mPEG$_{20,000}$-butanethiol, as prepared in Example 4B, was then added to the dialyzed solution of intermediate conjugate, followed by mixing for one hour at room temperature and then overnight at 4° C., to thereby form the mPEG$_{20,000}$-PEG$_{2,000}$-GCSF conjugate. The product was characterized by SDS-PAGE and RP-HPLC.

This approach can be used to prepare other conjugates, using PEG-di-(4C-OPSS) and mPEG-4C-SH having other molecular weights, again where the PEG-di-(4C-OPSS) reagent is preferably of relatively low molecular weight.

Example 8b

PEGylation of G-CSF with PEG$_{2000}$-di-((CH$_2$)$_4$-orthopyridyl disulfide) and mPEG$_{30,000}$-butanethiol The procedure of Example 8a was repeated using corresponding amounts of PEG$_{2000}$-di-((CH$_2$)$_4$-orthopyridyl disulfide) and mPEG$_{30,000}$-butanethiol, to obtain the corresponding mPEG$_{30,000}$-PEG$_{2000}$-GCSF conjugate.

Other conjugates can be similarly prepared using PEG-di-(4C-OPSS) and mPEG-4C-SH having other molecular weights.

Examples 9-10 below differ from each other in that the low molecular weight PEG species of Example 9 contains a four-carbon hydrophilic linker of the invention, while that of Example 10 contains only a two-carbon linker. It can be seen that the linker of the invention provides significantly greater yields of conjugate.

Example 9

PEGylation of G-CSF with PEG$_{2000}$-di-((CH$_2$)$_4$-orthopyridyl disulfide) and branched PEG2$_{40,000}$-thiol

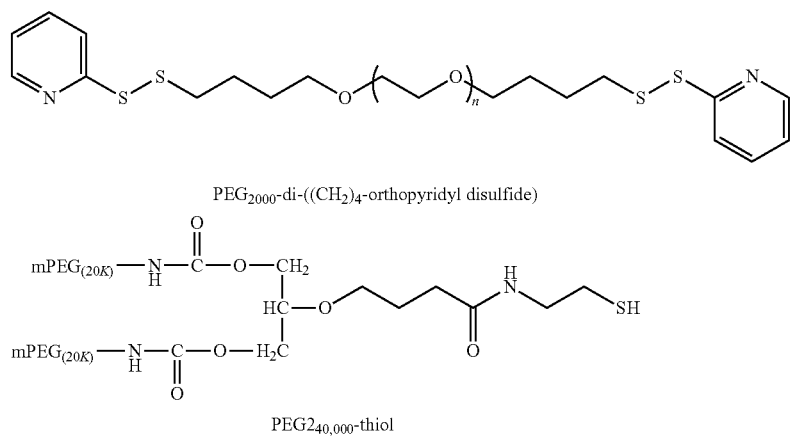

Again, these examples employ an approach involving initial attachment of a polymeric reagent having a relatively small molecular weight (in this Example, PEG$_{2,000}$-di-(4C-OPSS)) to a G-CSF moiety, followed by attachment of a relatively large molecular weight polymeric reagent (in this Example, branched PEG2$_{40,000}$-thiol) to residue of the PEG$_{2,000}$-di-(4C-OPSS) reagent, through another disulfide linkage.

PEG$_{2,000}$-di-(4C-OPSS) as prepared in Example 2, stored at $-20°$ C. under argon, was warmed to ambient temperature. A fifty-fold excess (relative to the amount of G-CSF in a measured aliquot of stock G-CSF solution) of the warmed PEG$_{20,000}$-di-(4C-OPSS) was dissolved in DMSO to form a 10% reagent solution. The 10% reagent solution was quickly added to the aliquot of stock G-CSF solution (0.4 mg/ml in sodium phosphate buffer, pH 7.0) and mixed well. The solution was placed on a RotoMix (Type 48200, Thermolyne, Dubuque Iowa) and allowed to mix for one hour at 37° C., then for two hours at room temperature. After the reaction was complete, the reaction solution was dialyzed against sodium phosphate buffer, pH 7.0, to remove excess PEG$_{20,000}$-di-(4C-OPSS).

A seventy five-fold excess (relative to G-CSF) of PEG2$_{40,000}$-thiol (Nektar Therapeutics) was then added to the dialyzed conjugate solution, followed by mixing for three hours at room temperature and then overnight at 4° C., to form a PEG2$_{40,000}$-PEG$_{2,000}$-G-CSF conjugate. The conjugate was characterized by SDS-PAGE and RP-HPLC. The final yield of conjugate obtained was 35%.

Example 10 (Comparative)

PEGylation Reaction of G-CSF with PEG$_{2000}$-di-orthopyridyl disulfide) and PEG2$_{40,000}$-thiol

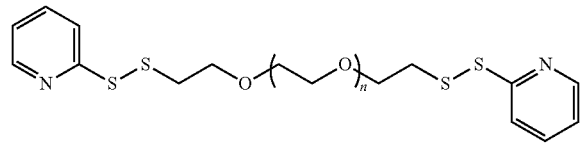

PEG$_{2000}$-di-((CH$_2$)$_2$-orthopyridyl disulfide)

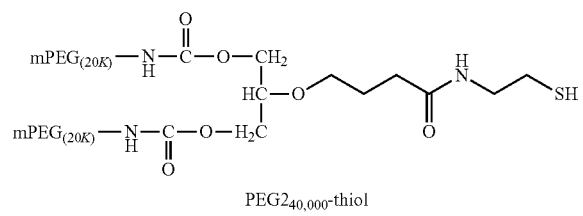

PEG2$_{40,000}$-thiol

The reaction procedure of Example 10 was essentially duplicated, using a low molecular weight PEG thiol reagent having a two-carbon rather than a four-carbon linker.

Accordingly, PEG$_{2,000}$-di-(2C-OPSS) from Nektar Therapeutics, stored at −20° C. under argon, was warmed to ambient temperature. A fifty-fold excess (relative to the amount of G-CSF in a measured aliquot of stock G-CSF solution) of the reagent was dissolved in DMSO to form a 10% solution. This solution was quickly added to the aliquot of stock G-CSF solution (0.4 mg/ml in sodium phosphate buffer, pH 7.0) and mixed well. The reaction solution was placed on a RotoMix (Type 48200, Thermolyne, Dubuque Iowa) and was allowed to mix for one hour at 37° C., then for two hours at room temperature. After the reaction was complete, the reaction solution was dialyzed against sodium phosphate buffer, pH 7.0, to remove excess PEG$_{2,000}$-di-(2C-OPSS).

A seventy-fold excess (relative to G-CSF) of branched PEG2$_{40,000}$-thiol (Nektar Therapeutics) was added to the dialyzed conjugate solution, followed by mixing for three hour at room temperature and overnight at 4° C. However, SDS-PAGE and RP-HPLC analysis showed no detectable amount of the desired PEG2$_{40,000}$-PEG$_{2,000}$-G-CSF conjugate.

Evidence suggests that the ethylene (C2)-linked PEG-OPSS reagent undergoes reductive cleavage to effectively destroy the reagent before it reacts with the target protein. The butylene (C4)-linked reagent is more stable to such cleavage and thereby survives to give a much higher yield of conjugate.

Example 11

Preparation of mPEG$_{5000}$-CH$_2$—CH$_2$—CH$_2$—CH(CH$_3$)-orthopyridyl disulfide (mPEG-(α-methyl)4C-OPSS 5 KDa)

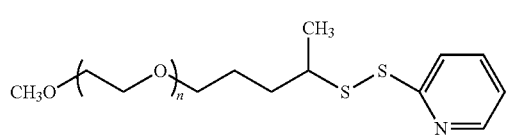

1-Methyl-4-bromo-1-butanol

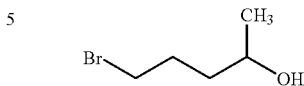

2-Methyltetrahydrofuran (10.14 g, 0.0834 mol) was dissolved in chloroform (72 ml), and tetraethylammonium bromide (18.4 g, 0.0876 mol) was added. Boron trifluoride-diethyl etherate (11.12 ml, 0.0876 mol) was then added dropwise over 15 min, and the solution was stirred overnight at room temperature. The solution was cooled to 0-5° C. and washed with saturated aqueous NaHCO$_3$ (80 ml). The organic layer was separated, washed with water (80 ml) and saturated aqueous NaCl (80 ml), and dried with anhydrous Na$_2$SO$_4$. The solvent was removed by distillation, giving 9.5 g of pale yellow viscous liquid.

NMR (d$_6$-DMSO): 1.04 ppm (d, —CH$_3$—, 3H), 1.43 ppm (b, —CH$_2$—CH(CH$_3$)—OH, 2H), 1.84 ppm (m, —CH$_2$—CH$_2$—CH(CH$_3$)—OH, 2H), 3.53 ppm (t, —CH$_2$Br, 2H), 3.60 ppm (m, —CH$_2$—CH(CH$_3$)—OH, 1H), 4.41 ppm (bs, —OH, 1H).

1-Bromo-4-methyl-4-benzyloxybutane

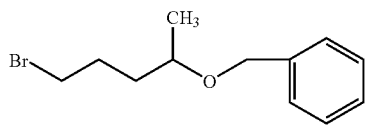

To a solution of 1-methyl-4-bromo-1-butanol (9.0 g, 0.05384 mol) and benzyl 2,2,2-trichloroacetimidate (16.3 g, ) in a mixture of anhydrous cyclohexane (100 ml) and anhydrous dichloromethane (50 ml) cooled to 0° C., trifluoromethanesulfonic acid (1.0 ml) was added, and the mixture was stirred overnight at room temperature under argon. The mixture was filtered, washed with a saturated solution of NaHCO$_3$ (250 ml) and deionized water (250 ml), and dried with anhydrous Na$_2$SO$_4$. The solvents were removed by distillation under reduced pressure. The crude product (9.2 g) was subjected to vacuum distillation, giving 7.2 g of colorless viscous liquid.

NMR (d$_6$-DMSO): 1.14 ppm (d, —CH$_3$—, 3H), 1.57 ppm (m, —CH$_2$—CH(CH$_3$)—OH, 2H), 1.88 ppm (m, —CH$_2$—CH$_2$—CH(CH$_3$)—OH, 2H), 3.53 ppm (bm, —CH$_2$Br, 2H and —CH$_2$—CH(CH$_3$)—OH, 1H), 4.46 ppm (m, —CH$_2$-benzyl, 2H), 7.32 ppm (m, C$_6$H$_5$—, benzyl, 5H).

mPEG$_{5000}$-4-methyl-4-benzyloxybutane

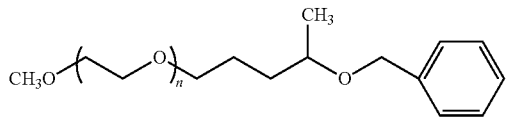

To an azeotropically dried solution of mPEG$_{5000}$ (20.0 g, 0.004 mole) (NOF Corporation) in anhydrous toluene (200 ml), a 1.0M solution of potassium tert-butoxide in tert-butanol (16.0 ml, 0.0160 mole) and 1-bromo-4-methyl-4-benzyloxybutane (3.10 g, 0.012 mole) were added. The reaction mixture was stirred for 20 hours at 70° C. under nitrogen. The resulting mixture was filtered and concentrated under vacuum to dryness. The crude product was dissolved in 30 ml of dichloromethane and precipitated with 500 ml of isopropanol at 0-5° C. The final product was collected through vacuum filtration and dried under vacuum overnight. Yield: 17.4 g.

NMR ($d_6$-DMSO): 1.14 ppm (d, —$CH_3$, 3H), 1.57 ppm (m, —$\underline{CH_2}$—CH($CH_3$)—OH, 2H), 1.88 ppm (m, —$\underline{CH_2}$—$\underline{CH_2}$—CH($CH_3$)—OH, 2H), 3.24 ppm (s, —$OCH_3$, 3H), 3.51 ppm (s, polymer backbone), 4.46 ppm (m, —$CH_2$-benzyl, 2H), 7.32 ppm (m, $C_6H_5$—, benzyl, 5H).

mPEG$_{5000}$-4-methyl-4-butanol

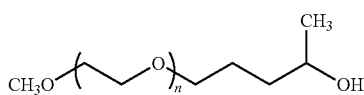

A mixture of mPEG$_{5000}$-4-methyl-4-benzyloxybutane (15.0 g, 0.00300 mole), ethyl alcohol (150 ml), and palladium (10% on active carbon, 1.5 g) was hydrogenated overnight under 45 psi of hydrogen. The mixture was filtered and the solvent was removed by distillation under reduced pressure. The crude product was dissolved in dichloromethane (25 ml) and precipitated with 400 ml isopropyl alcohol at 0-5° C. The product was filtered off and dried under reduced pressure. Yield: 13.1 g.

NMR ($d_6$-DMSO): 1.14 ppm (d, —$CH_3$, 3H), 1.57 ppm (m, —$\underline{CH_2}$—CH($CH_3$)—OH, 2H), 1.88 ppm (m, —$\underline{CH_2}$—$\underline{CH_2}$—CH($CH_3$)—OH, 2H), 3.24 ppm (s, —$OCH_3$, 3H), 3.51 ppm (s, polymer backbone), 4.45 ppm (bs, —OH, 1H).

mPEG$_{5000}$-4-methyl-4-methanesulfonylbutane

A solution of mPEG$_{5000}$-4-methyl-4-butanol (10.0 g, 0.0020 mole) in toluene (100 ml) was azeotropically dried by distilling off toluene under reduced pressure. The dried mPEG$_{5000}$-4-methyl-4-butanol was dissolved in a mixture of anhydrous toluene (100 ml) and anhydrous dichloromethane (20 ml). Triethylamine (0.9 ml, 0.0030 mole) and methanesulfonyl chloride (0.45 ml, 0.0026 mole) were added, and the mixture was stirred overnight at room temperature under nitrogen. The solvents were removed by distillation under reduced pressure. The residue was dissolved in dichloromethane (15 ml), and 250 ml isopropyl alcohol was added. The precipitated product was filtered and dried under vacuum to yield 8.9 g of the white solid powder.

NMR ($d_6$-DMSO): 1.40 ppm (d, —$CH_3$, 3H), 1.57 ppm (m, —$\underline{CH_2}$—CH($CH_3$)-mesylate, 2H), 1.88 ppm (m, —$\underline{CH_2}$—$\underline{CH_2}$—CH($CH_3$)-mesylate, 2H), 3.17 ppm (s, —$CH_3$, mesylate, 3H), 3.24 ppm (s, —$OCH_3$, 3H), 3.51 ppm (s, polymer backbone), 4.00 ppm (m, —CH-mesylate, 1H).

mPEG$_{5000}$-4-methyl-4-butanethiol

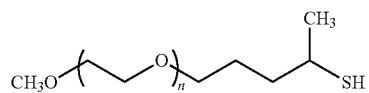

To a solution of mPEG$_{5000}$-4-methyl-4-methanesulfonylbutane (8.0 g, 0.0016 mol) in anhydrous ethyl alcohol (80 ml), thiourea (1.24 g, 0.0163 mol) was added, and the mixture was stirred overnight at 78° C. under argon. The solvent was removed by distillation under reduced pressure, and the residue was dissolved in 1% aqueous NaOH (84 ml). This solution was heated for 2.5 h at 85° C. under argon. After cooling the solution to 35° C., the pH was adjusted to 3 with 10% phosphoric acid. NaCl (24 g) was added, and the product was extracted with dichloromethane. The extract was dried with anhydrous sodium sulfate, and the product was precipitated with cold ethyl ether. Yield 7.3 g.

NMR (CDCl$_3$): 1.24 ppm (d, —$CH_3$, 3H), 1.38 ppm (m, —$\underline{CH_2}$—CH($CH_3$)—SH, 2H), 1.54 ppm (d, —CH—$\underline{SH}$, 1H), 1.88 ppm (m, —$\underline{CH_2}$—$\underline{CH_2}$—CH($CH_3$)—SH, 2H), 2.83 ppm (m, —$CH_2$—$\underline{CH}$($CH_3$)—SH, 1H), 2.05 ppm (m, —$\underline{CH_2}$—CH($CH_3$)—S—S—CH($CH_3$)—$\underline{CH_2}$—, 4H, 0.7 mol %), 3.38 ppm (s, —$OCH_3$, 3H), 3.64 ppm (s, PEG backbone).

The NMR data, above, indicated that the product contained a very small amount (0.7 mol % by NMR) of disulfide-linked dimer, formed by oxidation of thiol groups. No further purification of the thiol was required.

mPEG$_{5000}$-$CH_2$—$CH_2$—$CH_2$—CH($CH_3$)—OPSS

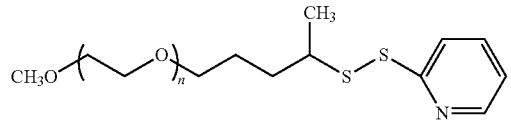

To a solution of mPEG$_{5000}$-4-methyl-4-butanethiol (2.0 g, 0.0004 mol) in anhydrous methyl alcohol (40 ml), 2,2'-dipyridyl disulfide (0.18 g, 0.00082 mol) was added, and the mixture was stirred for 4 h at room temperature under argon. The solvent was removed by distillation under reduced pressure, the residue was dissolved in dichloromethane (5 ml), and the product was precipitated with 50 ml of cold ethyl ether. Yield 1.7 g.

NMR (CDCl$_3$): 1.34 ppm (d, —$CH_3$, 3H), 1.68 ppm (m, —$CH_2$—$CH_2$—CH($CH_3$)—SH, 2H), 1.88 ppm (m, —$CH_2$—$\underline{CH_2}$—CH($CH_3$)—SH, 2H), 3.38 ppm (s, —$OCH_3$, 3H), 3.64 ppm (s, PEG backbone), 7.12, 7.68, 7.75, & 8.47 ppm (4 m, pyridyl protons, 4H).

The invention claimed is:

1. A water-soluble polymeric reagent of the structure:

POLY-[Y—S—W]$_x$ wherein:
POLY is a water soluble polymer;
Y has the formula —(CR$^1$R$^2$)n-, where n is 3 to 8, and each of R$^1$ and R$^2$ is independently selected from hydrogen, lower alkyl, lower alkenyl, and a non-interfering substituent, where two groups R$^1$ and R$^2$ on different carbon atoms may be linked to form a cycloalkyl or aryl group;
S is a sulfur atom attached to an sp$^3$ hybridized carbon of Y;

S—W is a thiol, protected thiol, or thiol-reactive thiol derivative;

x=1-25; and if POLY is a linear polyethylene glycol, x=1, and Y is a linear alkyl chain then POLY has a molecular weight of at least 500, wherein when S—W is the disulfide linkage ortho-pyridyl disulfide and POLY is a linear polyethylene glycol, at least one $R^1$ on a carbon adjacent to said disulfide linkage is lower alkyl.

2. The reagent of claim 1, wherein x is 1 or 2.

3. The reagent of claim 1, wherein POLY is a polyethylene glycol.

4. The reagent of claim 1, wherein S—W is a thiol-reactive thiol derivative.

5. The reagent of claim 4, wherein S—W is ortho-pyridyl disulfide (OPSS).

6. The reagent of claim 4, wherein said polyethylene glycol has a molecular weight of 1000 to about 100,000 Daltons and a morphology selected from linear, branched, forked, and multiarmed.

7. The reagent of claim 1, wherein Y is selected from the group consisting of $C_4$-$C_8$ alkylene, $C_5$-$C_8$ cycloalkylene, and combinations thereof.

8. The reagent of claim 1, wherein n is 3 to 6, and each of $R^1$ and $R^2$ is independently selected from hydrogen and methyl.

9. The reagent of claim 1, wherein each of $R^1$ and $R^2$ is hydrogen with the exception of $R^1$ on a carbon adjacent said sulfur atom, said $R^1$ being lower alkyl.

10. The reagent of claim 9, wherein said lower alkyl is methyl or ethyl.

11. The reagent of claim 10, wherein said lower alkyl is methyl.

12. The reagent of claim 1, wherein two groups $R^1$ and $R^2$ on different carbon atoms are linked to form a cycloalkyl or aryl group.

13. The reagent of claim 12, wherein Y comprises a cyclopentyl or cyclohexyl group.

14. The reagent of claim 1, wherein said non-interfering substituents are selected from the group consisting of $C_3$-$C_6$ cycloalkyl, halo, cyano, lower alkoxy, and phenyl.

15. A water-soluble polymeric reagent of the structure:

POLY-[Y—S—W]$_x$ wherein:

POLY is a water soluble polymer;

Y has the formula —$(CR^1R^2)n$-, where n is 3 to 8, and each of $R^1$ and $R^2$ is independently selected from hydrogen, lower alkyl, lower alkenyl, and a non-interfering substituent, where two groups $R^1$ and $R^2$ on different carbon atoms may be linked to form a cycloalkyl or aryl group;

S is a sulfur atom attached to an $sp^3$ hybridized carbon of Y;

x is 2-25; and

S—W is a thiol, protected thiol, or thiol-reactive thiol derivative, wherein when S—W is the disulfide linkage ortho-pyridyl disulfide and POLY is a linear polyethylene glycol, at least one $R^1$ on a carbon adjacent to said disulfide linkage is lower alkyl.

16. The reagent of claim 15, where n is 3 to 6.

17. The reagent of claim 15, wherein each of $R^1$ and $R^2$ is hydrogen.

18. The reagent of claim 15, wherein for at least one Y, each of $R^1$ and $R^2$ is hydrogen with the exception of $R^1$ on a carbon adjacent said sulfur atom, said $R^1$ being lower alkyl.

19. The reagent of claim 18, wherein x is 2.

* * * * *

UNITED STATES PATENT AND TRADEMARK OFFICE
CERTIFICATE OF CORRECTION

Page 1 of 1

PATENT NO.       : 7,851,565 B2
APPLICATION NO.  : 11/316051
DATED            : December 14, 2010
INVENTOR(S)      : Antoni Kozlowski et al.

It is certified that error appears in the above-identified patent and that said Letters Patent is hereby corrected as shown below:

On the cover page of the patent in field 60, please add after December 21, 2004

--and provisional application No. 60/705,968, filed on August 4, 2005-- so that field 60 will read

Provisional application No. 60/639,823, filed on December 21, 2004 and provisional application No. 60/705,968, filed on August 4, 2005.

Signed and Sealed this
Eighth Day of February, 2011

David J. Kappos
*Director of the United States Patent and Trademark Office*